United States Patent
McDevitt et al.

(10) Patent No.: US 7,127,771 B2
(45) Date of Patent: *Oct. 31, 2006

(54) DENTAL WIPE

(75) Inventors: Jason P. McDevitt, Alpharetta, GA (US); Michael S. Brunner, Roswell, GA (US); Jark C. Lau, Roswell, GA (US); Jaeho Kim, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/603,043

(22) Filed: Jun. 24, 2003

(65) Prior Publication Data

US 2005/0071938 A1  Apr. 7, 2005

Related U.S. Application Data

(63) Continuation of application No. 09/826,411, filed on Apr. 4, 2001.

(60) Provisional application No. 60/257,173, filed on Dec. 20, 2000, provisional application No. 60/195,517, filed on Apr. 6, 2000, provisional application No. 60/195,071, filed on Apr. 6, 2000, provisional application No. 60/194,929, filed on Apr. 6, 2000, provisional application No. 60/195,072, filed on Apr. 6, 2000, provisional application No. 60/194,930, filed on Apr. 6, 2000.

(51) Int. Cl.
*A47K 7/02* (2006.01)
*A61C 15/00* (2006.01)

(52) U.S. Cl. ............... 15/227; 15/104.94; 132/323; 2/21

(58) Field of Classification Search ............... 15/167.1, 15/227, 104.94; 2/21; 132/323, 309, 327; D28/65, 66
See application file for complete search history.

(56) References Cited

U.S. PATENT DOCUMENTS

| | | | |
|---|---|---|---|
| 2,041,262 A * | 5/1936 | Ness ..................... 15/188 |
| 2,076,681 A | 4/1937 | Steinmayer |
| 2,122,482 A | 7/1938 | Marr et al. |
| 2,179,614 A | 11/1939 | Cohen |
| 2,599,191 A * | 6/1952 | Meunier ................ 15/167.1 |
| 2,646,796 A | 7/1953 | Scholl |
| 2,966,691 A * | 1/1961 | Cameron ............... 15/104.94 |
| 3,070,102 A | 12/1962 | MacDonald |
| 3,280,420 A | 10/1966 | Wanzenberg |
| 3,298,507 A | 1/1967 | Micciche |

(Continued)

FOREIGN PATENT DOCUMENTS

DE  19620487 A1  11/1997

(Continued)

OTHER PUBLICATIONS

Medical Textiles, Nov. 1999 "Crimped Bristle Toothbrush". "Nonwoven Removes Stains", "Dental Floss".

(Continued)

*Primary Examiner*—Gladys JP Corcoran
*Assistant Examiner*—Laura C Guidotti
(74) *Attorney, Agent, or Firm*—Dority & Manning, P.A.

(57) ABSTRACT

An oral cleaning device that can fit onto a human finger is provided. The oral cleaning device, or dental wipe, is at least partially made from an elastomeric material, such as an elastomeric nonwoven, so that the wipe can more aptly fit onto a finger. Furthermore, the wipe, in some instances, can possess a barrier that is liquid-impervious, but vapor-permeable so that the finger of a user is more comfortable during cleaning. Various additives can be applied to the wipe to aid in the cleaning process.

23 Claims, 10 Drawing Sheets

U.S. PATENT DOCUMENTS

| | | |
|---|---|---|
| 3,338,992 A | 8/1967 | Kinney |
| 3,341,394 A | 9/1967 | Kinney |
| 3,348,541 A | 10/1967 | Loebeck |
| 3,485,706 A | 12/1969 | Evans |
| 3,502,763 A | 3/1970 | Hartman |
| 3,542,615 A | 11/1970 | Dobo et al. |
| 3,589,823 A | 6/1971 | Hendrickson |
| 3,692,618 A | 9/1972 | Dorschner |
| 3,696,821 A * | 10/1972 | Adams, IV ............... 132/324 |
| 3,802,817 A | 4/1974 | Matsuki et al. |
| 3,849,241 A | 11/1974 | Butin et al. |
| 3,853,412 A | 12/1974 | Griffin |
| 3,855,046 A | 12/1974 | Hansen et al. |
| 3,902,509 A | 9/1975 | Tundermann et al. |
| 3,905,113 A | 9/1975 | Jacob |
| 3,952,867 A | 4/1976 | McCord |
| 3,982,298 A * | 9/1976 | Ota ......................... 15/106 |
| 4,041,203 A | 8/1977 | Brock et al. |
| 4,084,586 A | 4/1978 | Hettick |
| 4,121,312 A | 10/1978 | Penney |
| 4,269,181 A | 5/1981 | Delannoy |
| 4,323,534 A | 4/1982 | DesMarais |
| 4,333,979 A | 6/1982 | Sciaraffa et al. |
| 4,340,563 A | 7/1982 | Appel et al. |
| 4,414,970 A | 11/1983 | Berry |
| 4,616,374 A | 10/1986 | Novogrodsky |
| 4,617,694 A | 10/1986 | Bori |
| 4,643,791 A | 2/1987 | Jurrius et al. |
| 4,655,760 A | 4/1987 | Morman et al. |
| 4,657,802 A | 4/1987 | Morman et al. |
| 4,663,220 A | 5/1987 | Wisneski et al. |
| 4,665,901 A | 5/1987 | Spector |
| 4,707,398 A | 11/1987 | Boggs |
| 4,720,415 A | 1/1988 | Vander Wielen et al. |
| 4,724,184 A | 2/1988 | Killian et al. |
| 4,741,949 A | 5/1988 | Morman et al. |
| 4,766,029 A | 8/1988 | Brock et al. |
| 4,781,966 A | 11/1988 | Taylor |
| 4,789,699 A | 12/1988 | Kieffer et al. |
| 4,795,668 A | 1/1989 | Krueger et al. |
| 4,803,117 A | 2/1989 | Daponte |
| 4,820,572 A | 4/1989 | Killian et al. |
| 4,828,556 A | 5/1989 | Braun et al. |
| 4,834,738 A | 5/1989 | Kielpikowski et al. |
| 4,875,247 A | 10/1989 | Berg |
| 4,884,581 A * | 12/1989 | Rescigno ................... 128/869 |
| 4,923,742 A | 5/1990 | Killian et al. |
| 4,965,122 A | 10/1990 | Morman |
| 4,981,747 A | 1/1991 | Morman |
| 4,998,978 A | 3/1991 | Varum |
| 5,057,368 A | 10/1991 | Largman et al. |
| 5,068,941 A | 12/1991 | Dunn |
| 5,093,422 A | 3/1992 | Himes |
| 5,108,820 A | 4/1992 | Kaneko et al. |
| 5,108,827 A | 4/1992 | Gessner |
| 5,114,781 A | 5/1992 | Morman |
| 5,116,662 A | 5/1992 | Morman |
| 5,123,113 A | 6/1992 | Smith |
| 5,133,971 A | 7/1992 | Copelan et al. |
| 5,169,706 A | 12/1992 | Collier, IV et al. |
| 5,181,914 A | 1/1993 | Zook |
| 5,213,428 A | 5/1993 | Salman |
| 5,226,992 A | 7/1993 | Morman |
| 5,228,433 A | 7/1993 | Rosen |
| 5,277,976 A | 1/1994 | Hogle et al. |
| 5,280,661 A * | 1/1994 | Brown ....................... 15/214 |
| 5,283,924 A | 2/1994 | Kaminski et al. |
| 5,287,584 A | 2/1994 | Skinner |
| 5,294,482 A | 3/1994 | Gessner |
| 5,304,599 A | 4/1994 | Himes |
| 5,320,531 A | 6/1994 | Delizo-Madamba |
| 5,332,613 A | 7/1994 | Taylor et al. |
| 5,336,545 A | 8/1994 | Morman |
| 5,336,552 A | 8/1994 | Strack et al. |
| 5,348,153 A | 9/1994 | Cole |
| 5,356,005 A | 10/1994 | Burrello |
| 5,362,306 A | 11/1994 | McCarver et al. |
| 5,382,400 A | 1/1995 | Pike et al. |
| 5,389,202 A | 2/1995 | Everhart et al. |
| 5,445,825 A | 8/1995 | Copelan et al. |
| 5,464,688 A | 11/1995 | Timmons et al. |
| 5,466,410 A | 11/1995 | Hills |
| 5,474,525 A | 12/1995 | Blott |
| 5,486,381 A | 1/1996 | Cleveland et al. |
| 5,487,201 A | 1/1996 | Hansen et al. |
| 5,503,908 A | 4/1996 | Faass |
| 5,507,641 A | 4/1996 | Cline |
| 5,524,764 A | 6/1996 | Kaufman et al. |
| 5,529,665 A | 6/1996 | Kaun |
| 5,541,388 A | 7/1996 | Gadd |
| 5,591,510 A | 1/1997 | Junker et al. |
| 5,678,273 A | 10/1997 | Porcelli |
| 5,765,252 A | 6/1998 | Carr |
| 5,770,229 A | 6/1998 | Tanihara et al. |
| 5,794,774 A | 8/1998 | Porcelli |
| 5,804,021 A | 9/1998 | Abuto et al. |
| 5,834,002 A | 11/1998 | Athanikar |
| 5,911,319 A | 6/1999 | Porcelli et al. |
| 5,953,783 A * | 9/1999 | Hahn ....................... 15/167.1 |
| 6,019,773 A | 2/2000 | Denmark |
| 6,065,480 A * | 5/2000 | Mader ....................... 132/323 |
| 6,420,625 B1 | 7/2002 | Jones et al. |
| 6,898,819 B1 | 5/2005 | Tanaka et al. |
| 2002/0152538 A1 | 10/2002 | McDevitt et al. |
| 2003/0050589 A1 | 3/2003 | McDevitt et al. |

FOREIGN PATENT DOCUMENTS

| | | |
|---|---|---|
| EP | 0303528 | 7/1988 |
| FR | 2848535 A1 | 6/2004 |
| GB | 1046146 | 10/1966 |
| WO | WO 87/07122 | 12/1987 |
| WO | WO 92/03947 | 3/1992 |
| WO | WO 95/31154 | 11/1995 |
| WO | WO 99/55271 | 11/1999 |

OTHER PUBLICATIONS

Tetra Medical Supply Corp.; Product Information; Jan. 4, 2000; www.tetramed.com/dress.htm.

Spandage; Product Information; Jan. 4, 2000; spandage.com/main.htm.

FootSmark Products; Product Information-Toe Caps & DigiCushions; Jan. 4, 2000; www.footsmart.com.

U.S. Appl. No. 08/928,787 entitled "Breathable, liquid impermeable, Apertured Film/Nonwoven Laminate & Process For Making The Same".

JP05044165 English Abstract.

JP06205723 English Abstract.

JP06285108 English Abstract.

McDevitt, et al., U.S. Appl. No. 09/826,371, filed Apr. 4, 2001, Disposable Finger Sleeve For Appendages.

McDevitt, et al., U.S. Appl. No. 09/826,413, filed Apr. 4, 2001, Finger Glove.

* cited by examiner

DENTAL WIPE

RELATED APPLICATIONS

The present application is a continuation of U.S. patent application Ser. No. 09/826,411, filed on Apr. 4, 2001. This application is based upon and also claims priority to the following provisional applications:

U.S. Ser. No. 60/195,517, filed on Apr. 6, 2000; U.S. Ser. No. 60/195,071, filed on Apr. 6, 2000; U.S. Ser. No. 60/194,929, filed on Apr. 6, 2000; U.S. Ser. No. 60/195,072, filed on Apr. 6, 2000; U.S. Ser. No. 60/194,930, filed on Apr. 6, 2000; and U.S. Ser. No. 60/257,173, filed on Dec. 20, 2000.

BACKGROUND OF THE INVENTION

Teeth cleaning is regularly required to maintain dental hygiene. Various films and residues, such as plaque, can build up on teeth and gums over a period of time, thereby adversely affecting oral health. In the past, toothbrushes have been utilized to remove such films and residues. Conventional toothbrushes typically have two ends with one end being a handle and the other containing bristles designed to disrupt and remove plaque and other residues from the surfaces being cleaned.

Although conventional toothbrushes are useful in a wide variety of environments, in some circumstances, they are less than desirable. For example, some individuals desire to maintain dental hygiene by cleaning their teeth throughout the day. Unfortunately, many daily environments do not provide a setting which fosters or even allows such activity. Moreover, travelers and those working in office environments may not find it convenient to use a toothbrush during the day. For instance, toothbrushes are not generally well-suited to be carried by persons on a day-to-day basis because of their bulky shape and the need to have access to a restroom lavatory.

In response to this desire for more frequent dental hygiene and for a cleaning device that can be easily used in public, various portable toothbrushes have been developed. In particular, a number of finger-mounted teeth cleaning devices were developed that could be placed on or over a finger and wiped over the teeth and gums. These devices are typically small, portable, and disposable.

One example of such a disposable teeth cleaning device is described in U.S. Pat. No. 3,902,509 to Tundermann et al. This device is made of a high wet strength material, such as a woven or nonwoven fabric, laminated to or coated with, a water-impervious material. The water-impervious material could be a thermoplastic material, such as polypropylene. Additionally, various materials, such as flavoring materials, bacteriostats, dentrifices, or detergents could be applied to the device. To use the device, one could simply place it over a finger and rub the surface of the device over the surfaces of the teeth to remove food and plaque films.

A similar oral hygiene finger device was more recently described in U.S. Pat. No. 5,445,825 to Copelan et al. In particular, this device includes a packet of protective material that contains a membrane therein. The membrane could, for example, be made from a nonwoven cellulose fiber mat with an embossed striated texture. The device described in Copelan et al. is dry and utilizes only the moisture in a user's own mouth. This packet could also be made from foil or moisture-impervious sheet plastic material.

These teeth cleaning devices, although portable, often fail to remain tightly fitted on a user's finger during cleaning. However, some finger-mounted teeth cleaning devices were developed to contain an elastomeric material that could help prevent the device from slipping or falling off the user's finger during cleaning. Examples of such teeth cleaning devices are disclosed in U.S. Pat. No. 5,068,941 to Dunn; U.S. Pat. No. 5,348,153 to Cole; U.S. Pat. No. 5,524,764 to Kaufman et al.; and PCT Publication No. WO 95/31154 to Mittiga et al. Despite the apparent benefit of such elastic teeth cleaning devices, these devices remain deficient in a variety of ways. For instance, these devices are often difficult to process using high speed manufacturing techniques, thereby necessitating higher production costs. Moreover, these devices can also fail to adequately fit onto the finger of a user, can be allergenic to a user, and in some cases, lack an aesthetically pleasing appearance. In addition, these devices are often not suitable for application with various additives useful for cleaning teeth or otherwise improving oral hygiene. Furthermore, these devices are typically not breathable nor moisture-impervious.

Definitions

As used herein, the term "biconstituent fibers" refers to fibers which have been formed from at least two polymers extruded from the me extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes referred to as multiconstituent fibers. Fibers of this general type are discussed in, for example, U.S. Pat. Nos. 5,108,827 and 5,294,482 to Gessner. Biconstituent fibers are also discussed in the textbook *Polymer Blends and Composites* by John A. Manson and Leslie H. Sperling, copyright 1976 by Plenum Press., a division of Plenum Publishing Corporation of New York, IBSN 0-306-30831-2, at pages 273 through 277.

As used herein, the term "breathable" means pervious to water vapor and gases. In other words, "breathable barriers" and "breathable films" allow water vapor to pass therethrough. For example, "breathable" can refer to a film or laminate having water vapor transmission rate (WVTR) of at least about 300 $g/m^2/24$ hours measured using ASTM Standard E96-80, upright cup method, with minor variations as described in the following Test Procedure.

A measure of the breathability of a fabric is the water vapor transmission rate (WVTR) which, for sample materials, is calculated essentially in accordance with ASTM Standard E96-80 with minor variations in test procedure as set forth hereinbelow. Circular samples measuring three inches in diameter are cut from each of the test materials, and tested along with a control, which is a piece of ACEL-GARD" 2500 sheet from Celanese Separation Products of Charlotte, N.C. "CELGARD" 2500 sheet is a microporous polypropylene sheet. Three samples are prepared for each material. The test dish is a No. 60-1 Vapometer pan distributed by Thwing-Albert Instrument Company of Philadelphia, Pa. 100 milliliters of water is poured into each Vapometer pan and individual samples of the test materials and control material are placed across the open tops of the individual pans. Screw-on flanges are tightened to form a seal along the edges of the pan, leaving the associated test material or control material exposed to the ambient atmosphere over a 6.5 cm diameter circle having an exposed area of approximately 33.17 square centimeters. The pans are placed in a forced air oven at 100° F. (32° C.) for one hour to equilibrate. The oven is a constant temperature oven with external air circulating through it to prevent water vapor accumulation inside. A suitable forced air oven is, for example, a Blue M Power-O-Matic 600 oven distributed by Blue M Electric Company of Blue Island, Ill. Upon completion of the equilibration, the pans are removed from the oven, weighed and immediately returned to the oven. After 24 hours, the pans are removed from the oven and weighed again. The preliminary test water vapor transmission rate values are calculated as follows: Test WVTR'(grams weight loss over 24 hours)×(315.5 g/m²/24 hours).

The relative humidity within the oven is not specifically controlled. Under predetermined set conditions of 100° F. (32° C.) and ambient relative humidity, the WVTR for the "CELGARD" 2500 control has been s defined to be 5000 grams per square meter for 24 hours. Accordingly, the control sample was run with each test and the preliminary test values were corrected to set conditions using the following equation: WVTR'(test WVTR/control WVTR)× (5000 g/m²/24 hrs.).

As used herein, the term "conjugate fibers" refers to fibers Which have been formed from at least two polymers extruded from separated extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement, wherein one polymer is surrounded by another or may be a side by side arrangement, a pie arrangement or an "islands-in-the-sea" arrangement. Conjugate fibers are taught by U.S. Pat. No. 5,108,820 to Kaneko et al., and U.S. Pat. No. 4,795,668 to Krueger et al., U.S. Pat. No. 5,336,552 to Strack et al. Conjugate fibers are also taught in U.S. Pat. No. 5,382,400 to Pike et al. and may be used to produced crimp in the fibers by using the differential rates of expansion and contraction of the two (or more) polymers. Crimped fibers may also be produced by mechanical means and by the process of German Patent DT 25 13 251 A1. For two component fibers, the polymers may be present in ratios of 75/25, 50/50, 25/75, or any other desired ratios. In addition to fibers having a circular diameter, the fibers may also have distinct shapes such as those described in U.S. Pat. No. 5,277,976 to Hogle et al. U.S. Pat. No. 5,466,410 to Hill, U.S. Pat. No. 5,069,970 to Largman et al., and U.S. Pat. No. 5,057,368 to Largman et al.

As used herein, the terms "elastic" and "elastomeric" are generally used to refer to materials that, upon application of a force, are stretchable to a stretched, biased length which is at least about 125%, or one and one fourth times, unstretched length, and which will retract at least about 50% of its elongation upon release of the stretching, biasing force.

As used herein, the term "filament" refers to a type of fiber that is described as a continuous strand that has a large ratio of length to diameter, such as, for example, a ratio of 1000 or more.

As used herein, "meltblown fibers" refers to fibers formed by extruding a molten thermoplastic material through a plurality of fine, usually circular, die capillaries as molten threads or filaments into converging high velocity, usually hot, gas (e.g. air) streams which attenuate the filaments of thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited on a collecting surface.

As used herein, a "moisture barrier" refers to any material that is relatively impermeable to the transmission of fluids, i.e. a fabric having a moisture barrier can have a blood strikethrough ratio of 1.0 or less according to ASTM test method 22. As used herein, unless otherwise denoted, all ASTM test methods refer to the methods as they exist in 1999.

As used herein, the term "neck-bonded" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992, 4,981,747, 4,965,122, and 5,336,545, all to Morman, all of which are incorporated herein by reference thereto.

As used herein, the term "nonwoven web" refers to a web having a structure of individual fibers or threads which are interlaid, but not in an identifiable manner as in a knitted fabric. Nonwoven webs or fabrics have been formed from many processes, such as, for example, meltblowing processes, spunbonding processes, and bonded carded web processes. The basis weight of nonwoven fabrics is usually expressed in ounces of material per square yard (osy) or grams per square meter (gsm) and the fibers diameters are usually expressed in microns. (Note that to convert from osy to gsm, multiply osy by 33.91).

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 to Kinney, U.S. Pat. No. 3,341,394 to Kinney, U.S. Pat. No. 3,502,763 to Hartman, and U.S. Pat. No. 3,542,615 to Dobo et al. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "stretch-bonded laminate" refers to a composite material having at least two layers in which one layer is a nonelastic gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat No. 4,720,415 to Vander Wielen et al., which is incorporated herein by reference. Other composite elastic materials are described and disclosed in U.S. Pat. No. 4,789,699 to Kieffer et al., U.S. Pat. No. 4,781,966 to Taylor, U.S. Pat. No. 4,657,802 to Morman, and U.S. Pat. No. 4,655,760 to Morman et al., all of which are incorporated herein by reference thereto.

As used herein, the term "texturized" refers to a base web having projections from a surface of the web in the Z-direction. The projections can have a length, for instance, from about 0.1 mm to about 25 mm, particularly from about 0.1 mm to about 5 mm, and more particularly from about 0.1 mm to about 3 mm. The projections can take on many forms and can be, for instance, bristles, tufts, loop structures such as the loops used in hook and loop attachment structures, and the like.

SUMMARY OF THE INVENTION

The present invention is generally directed to an oral cleaning device. The oral cleaning device includes a hollow member having at least one open end for the insertion of a finger. The hollow member includes a base web and defines a cleaning surface, such as a texturized surface, configured to clean the teeth and gums of a user. The texturized surface can include looped bristles, elevated tufts, or can be made from crimped fibers.

In accordance with the present invention, any material commonly used in the art to manufacture cloths, such as wipes, can be used as the base web. In particular, the base web of the present invention is typically made from a nonwoven web. Alternatively, the base web can include a woven material, such as a knitted material. More particularly, the base web of the present invention can be made from pulp fibers, synthetic fibers, thermomechanical pulp, or mixtures thereof such that the web has cloth-like properties. For instance, the base web can be made from various types of fibers, including meltblown, spunbond, bonded carded, bicomponent, and crimped fibers. Various laminates, such as elastic and film laminates, can also be used in the base web. For instance, suitable elastic laminates can include stretch-bonded and neck-bonded laminates.

In general, the dental wipe of the present invention can have various structures. For instance, in one embodiment, the dental wipe can have a unitary structure. In particular, the dental wipe having a unitary structure can comprise an elastic nonwoven material such that the base web can possess form-fitting properties to help the wipe effectively fit onto a finger, while also remaining breathable.

Besides a unitary structure, the dental wipe of the present invention can be made from different panels or sections. The panels or sections can be attached together by an adhesive, through stitching or by thermal bonding. The different panels or sections can be made from the same material or can be made from a different material. For example, in one embodiment, the dental wipe can include an elastic component and a non-elastic component. The non-elastic component can be attached to the elastic component in a manner that allows the elastic component to be stretched and contracted for providing the dental wipe with form-fitting properties.

In one embodiment, the dental wipe can include a first panel attached to a second panel. The first panel can include an elastic component while the second panel can include a non-elastic component. The first panel and the second panel can be connected together in any suitable manner. For example, the panels can be bonded in a way that forms a pair of seams. If desired, the attached panels can be inverted so that the seams are located on the inside of the dental wipe.

As described above, the dental wipe can further include an abrasive surface to facilitate cleaning. The abrasive surface can be made from various texturized materials. For example, as stated above, in one embodiment, the base web includes looped bristles on at least a portion of the cleaning surface. The loop bristles can have a size or height less than about 20 mm, particularly from about 1 to about 5 mm, and more particularly from about 1.5 to about 3.5 mm. As used herein, the size or height of a loop bristle refers to the size or height of the bristle in an extended state, as opposed to a relaxed state. The loop bristles can be oriented in columns, in rows or in any other suitable pattern or can be randomly arranged on the cleaning surface. The loops can be positioned perpendicular to the surface or at any angle to the surface. Further, the loop bristles can be sparsely positioned with respect to each other or can be densely packed together.

The loop bristles can be formed according to various methods. For instance, a knitted or woven fabric containing loop bristles can be used. Alternatively, looped bristles can be needle-punched into a base web. Alternatively, the loop bristles can be formed through a hydroentangling process or can be formed through a molding process.

The loop bristles themselves can be formed from various types of yarns. For instance, the loop bristles can be formed from a multi-filament yarn, a monofilament yarn, or a spun yarn. Further, the yarn used to form the looped bristles can be texturized and/or can be shaped. A shaped yarn, for instance, can have a multi-lobal shape, which may provide increased friction for facilitating cleaning.

Besides looped bristles, the texturized surface of the dental wipe can be made from various other materials. For instance, the texturized surface can be made from a nonwoven web containing crimped fibers. In another alternative embodiment, the texturized surface can be made from a point unbonded material. The point unbonded material can define a plurality of elevated tufts. In one particular embodiment of the present invention, the tufts can have a height of at least 0.02 inches.

Furthermore, in accordance with the present invention, the dental wipe can also include a moisture barrier that is incorporated into or applied as a layer to the base web. In general, a moisture barrier refers to any barrier, layer, or film that is substantially impermeable to liquid water. In particular, the moisture barrier of the present invention can prevent the flow of liquid through the dental wipe so that a finger inserted therein remains dry when the wipe is being used. In some embodiments, the moisture barrier can remain breathable, i.e., permeable to vapors, such that a finger within the wipe is more comfortable. Examples of suitable moisture barriers can include films such as plastic films, fibrous materials, microporous films, laminates, and the like. In one embodiment, the moisture barrier can be a multi-layered laminate. The laminate can be made from nonwoven webs and/or films. For example, the moisture barrier can be a laminate including a nonwoven web attached to a vapor-permeable film.

In accordance with the present invention, various additives can also be applied, if desired, to the dental wipe during manufacturing and/or by the consumer. For example, cationic materials, such as chitosan (poly-N-acetylglucosamine), chitosan salts, cationic starches, etc., can be applied to the wipe of the present invention to help attract negatively charged bacteria and deleterious acidic byproducts that may be present on the teeth and gums of the user. Moreover, various other additives can also be applied. Examples of other suitable additives include, but are not limited to, dental agents, such as fluorides, peppermint oil, mint oil and alcohol mixtures; flavoring agents, such as xylitol; anti-microbial agents; polishing agents; hemostatic agents; surfactants; anti-ulcer components; and the like.

Additives can be applied to the wipe of the present invention in the form of an aqueous solution, non-aqueous solution (e.g., oil), lotions, creams, suspensions, gels, etc. When utilized, the aqueous solution can, for example, be coated, saturated, sprayed, or impregnated into the wipe. In some embodiments, the additives can be applied asymmetrically. Moreover, in some instances, it may be desired that the additives comprise less than about 80% by weight of the wipe, and in some embodiments, less than about 50% by weight of the wipe and particularly less than 10% by weight of the wipe.

It should be noted that any given range presented herein is intended to include any and all lesser included ranges. For example, a range of from 45–90 would also include 50–90; 45–80; 46–89 and the like. Thus, the range of 95% to 99.999% also includes, for example, the ranges of 96% to 99.1%, 96.3% to 99.7%, and 99.91 to 99.999%.

Various features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
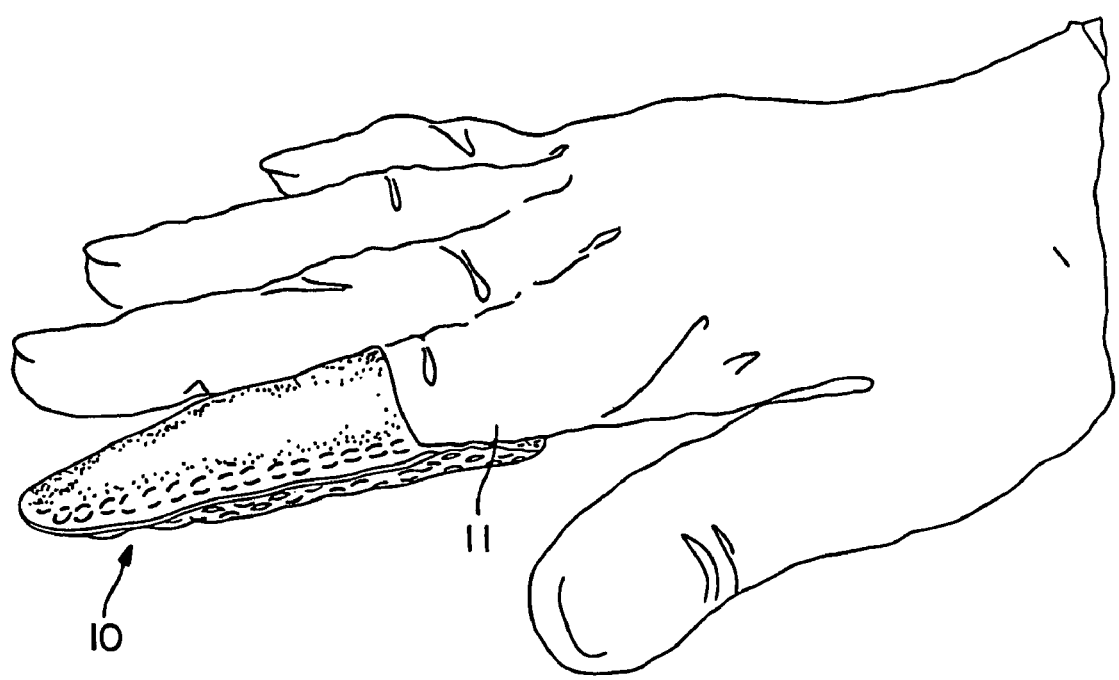
FIG. 1 is a perspective view of a dental wipe on a finger according to one embodiment of the present invention.

Repeated use of reference characters in the present specification and drawings is intended to represent the same or analogous features or elements of the invention.

DETAILED DESCRIPTION OF REPRESENTATIVE EMBODIMENTS

Reference now will be made in detail to the embodiments of the invention, one or more examples of which are set forth below. Each example is provided by way of explanation, not limitation of the invention. In fact, it will be apparent to those of ordinary skill in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claim and its equivalents.

In general, the present invention is directed to a dental wipe that can be more easily used during the day than toothbrushes. In particular, the present invention is directed to a dental wipe that can fit onto a human finger so that the teeth or gums of a person or animal can be cleaned by simply contacting the wipe therewith. For instance, the dental wipe of the present invention can be used by an individual to clean one's teeth or to clean the teeth of someone else, such as an infant, an elderly person, or a pet. Further, the dental wipe is particularly well suited for use by small children learning how to clean their teeth.

Besides being used to clean the teeth or gums of the user, the dental wipe of the present invention can also be used in other applications. For instance, the dental wipe can be used to clean various utensils, objects or surfaces and/or to polish the various items. For example, in one embodiment, the dental wipe can be used to polish silver. Thus, the term "dental wipe" as used herein should not be construed and limited solely to use as a device for cleaning one's teeth.

Dental wipes made in accordance with the present invention are generally constructed from disposable materials, such as nonwoven webs made from synthetic and/or pulp fibers. The dental wipe of the present invention typically includes a texturized surface adapted to scrub or clean the teeth or gums of a user. Further, the dental wipe can also include an elastic component for providing the wipe with form fitting properties. For instance, it has been discovered that by forming a dental wipe with an elastic component in accordance with the present invention, the resulting wipe can snugly fit onto a person's finger so that the wipe can more effectively remain on the finger throughout the cleaning process. Moreover, a dental wipe of the present invention can remain "breathable" to aid in a person's comfort during use, while also remaining capable of substantially inhibiting the transfer of liquids from the outer surface of the wipe to the person's finger. The transfer of liquids can be controlled using a liquid-impervious material and/or by using a highly liquid absorbent material.

A dental wipe of the present invention can generally be formed in a variety of ways. For instance, in one embodiment, the dental wipe can be formed as a unitary structure from a particular base web material, such as an elastomeric nonwoven base web material. Moreover, in another embodiment of the present invention, the dental wipe can be formed from two or more sections of base web material. Each section can be identical or different, depending on the desired characteristics of the dental wipe. For example, in one embodiment, the dental wipe is formed from two sections, wherein one section is formed from a texturized nonwoven material and the other section is formed from an elastomeric nonwoven material.

Referring to FIGS. 1–9, various embodiments of dental wipes made in accordance with the present invention are depicted. In general, a dental wipe of the present invention can be used to clean the oral cavity of a user by inserting the wipe onto a finger and maneuvering it within the oral cavity. In particular, as shown in FIG. 1, a dental wipe 10 can be placed over a finger 11 for cleaning.

Figure 8:
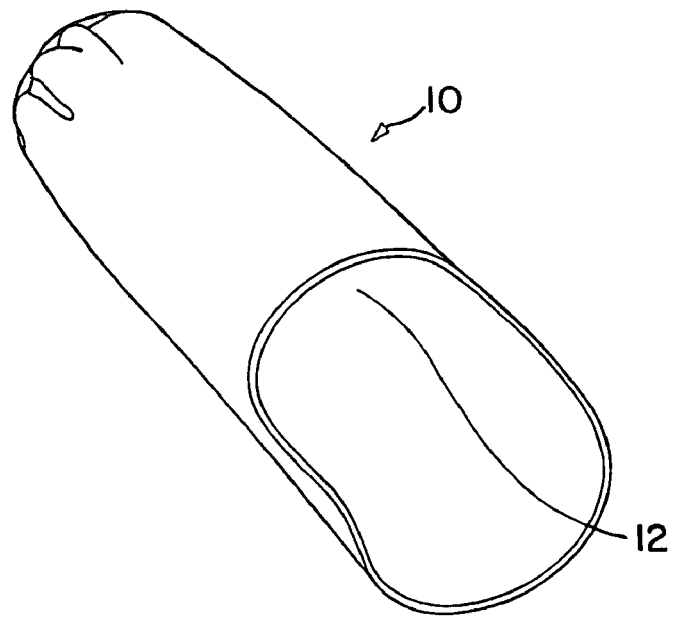
FIG. 8 is a perspective view of an embodiment of a dental wipe having a unitary structure.

One embodiment of a dental wipe of the present invention is depicted in FIG. 8. As shown, the dental wipe 10 is formed as a unitary structure from a single piece of fabric.

Figure 2:
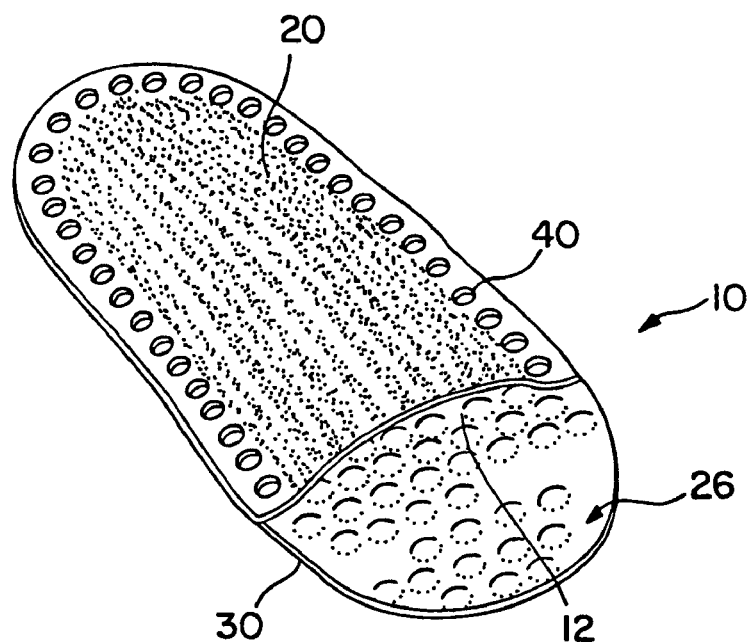
FIG. 2 is a perspective view of a two-sided dental wipe according to one embodiment of the present invention.
Figure 3:
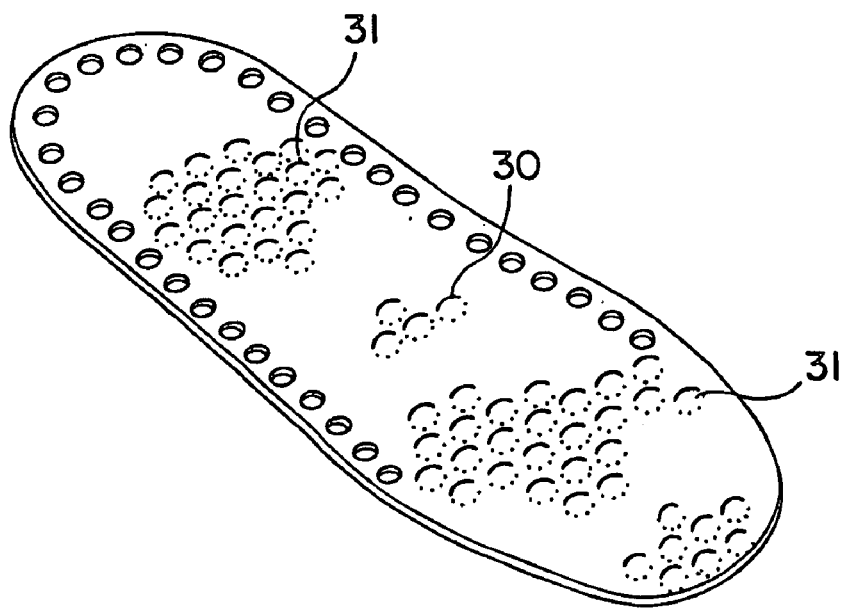
FIG. 3 is a perspective view of a bottom section of a two-sided dental wipe according to one embodiment of the present invention.
Figure 4:
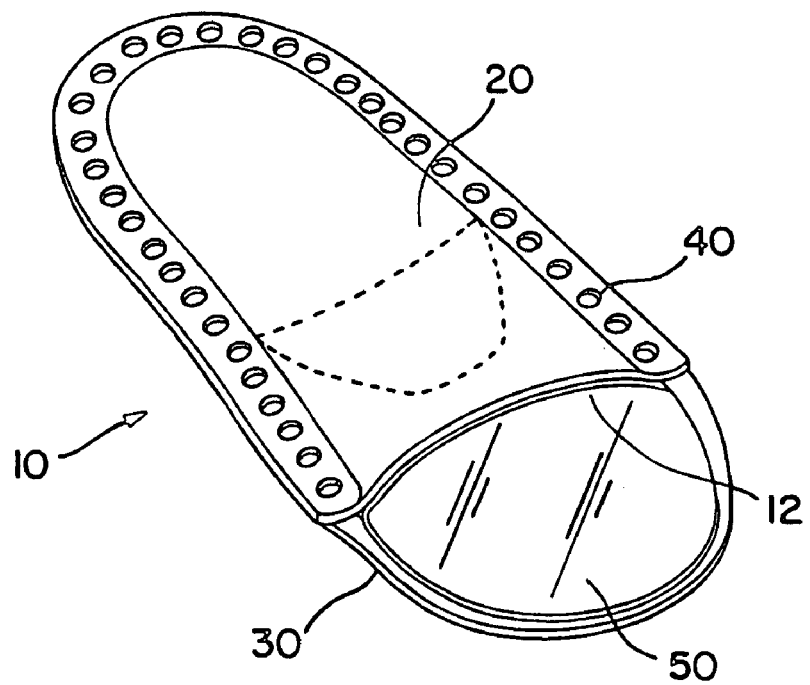
FIG. 4 is a perspective view of the two-sided dental wipe of FIG. 3.

Referring to FIGS. 2–4, another embodiment of a dental wipe of the present invention is depicted. As shown, in this embodiment, instead of a unitary structure, the dental wipe 10 is made from a first section 20 and a second section 30. Generally, one section of the dental wipe 10 can be bonded or attached to the other section in a finger-shaped pattern by any manner known in the art, such as by adhesive, thermal, or mechanical bonding, so that the connection of the sections can form a pocket for the insertion of a finger, as shown in FIG. 1. In the embodiment depicted in FIG. 2, for example, the first section 20 is attached in a finger-shaped pattern to the second section 30 at their respective outer edges via the seams 40 to form a dental wipe 10 having a pocket 12. Once each section is bonded or attached at the seams 40, the materials forming each of the sections 20 and 30 can then be cut adjacent to the seams such that the finger-shaped dental wipe 10 is formed.

In one embodiment of the present invention, in order to soften the feel of the seams of the dental wipe during use, a plurality of cuts can be made along the edges of the seam. The cuts, that can be referred to as microcuts, can be narrowly spaced along the seam. The cuts can be, for instance, less than 1 cm apart, particularly less than about 0.5 cm apart, and more particularly, less than about 1 mm apart. The cuts can extend substantially the entire width of the seam. For instance, the length of the cuts can be from about 0.1 cm to about 0.5 cm in length depending upon the particular application.

The microcuts can be formed into the seam using any suitable process. For instance, the cuts can be made using cutting dyes, laser technology, ultrasonic knives, and the like.

Figure 5:
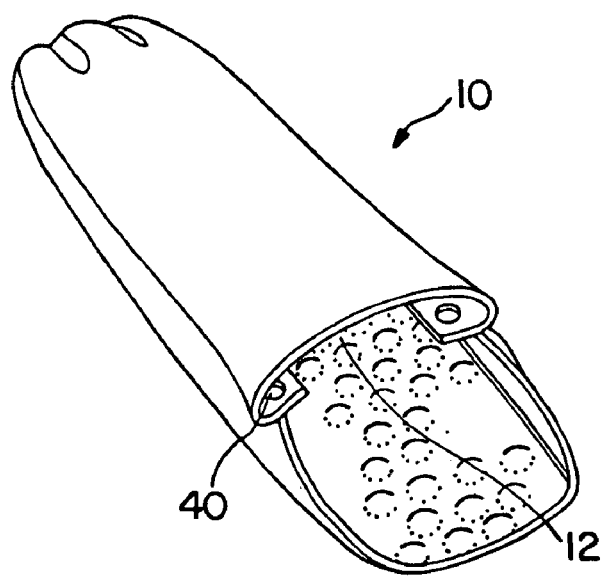
FIG. 5 is a perspective view of a dental wipe turned "inside-out" according to one embodiment of the present invention.
Figure 6:
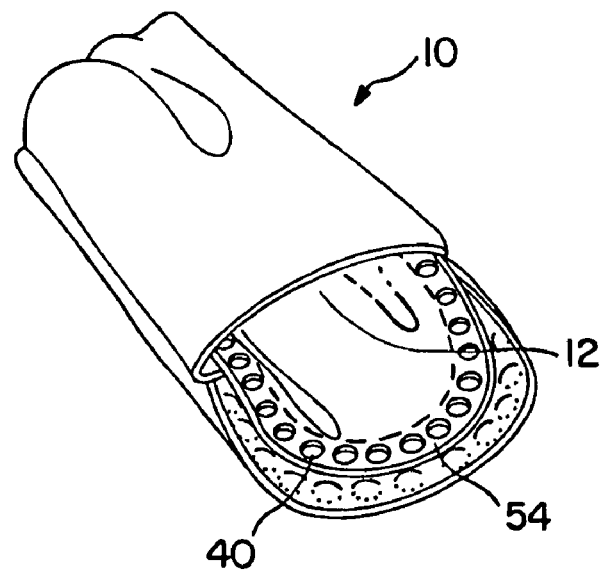
FIG. 6 is a perspective view of a dental wipe turned "inside-out" according to another embodiment of the present invention.

In some embodiments, as depicted in FIGS. 5–6, the dental wipe 10 can also be supplied in an inside-out configuration such that the seams 40 are located inside the pocket 12. For example, as shown in FIG. 6, the seams 40 of the dental wipe 10 can be pushed into the pocket 12 such that the seams 40 remain on the inside of the wipe 10, as depicted in FIG. 5. This "inside-out" position, as shown in FIG. 5, can provide the dental wipe with improved aesthetics. Moreover, the seams in the inside-out position can also provide a better fit by providing more friction applied to the finger. In addition, in some embodiments, this "inside-out" position can enable the dental wipe 10 to be more resistant to "flattening out" during use. Further, inverting the dental wipe can prevent the seams from causing irritation in the mouth when used.

Figure 10:
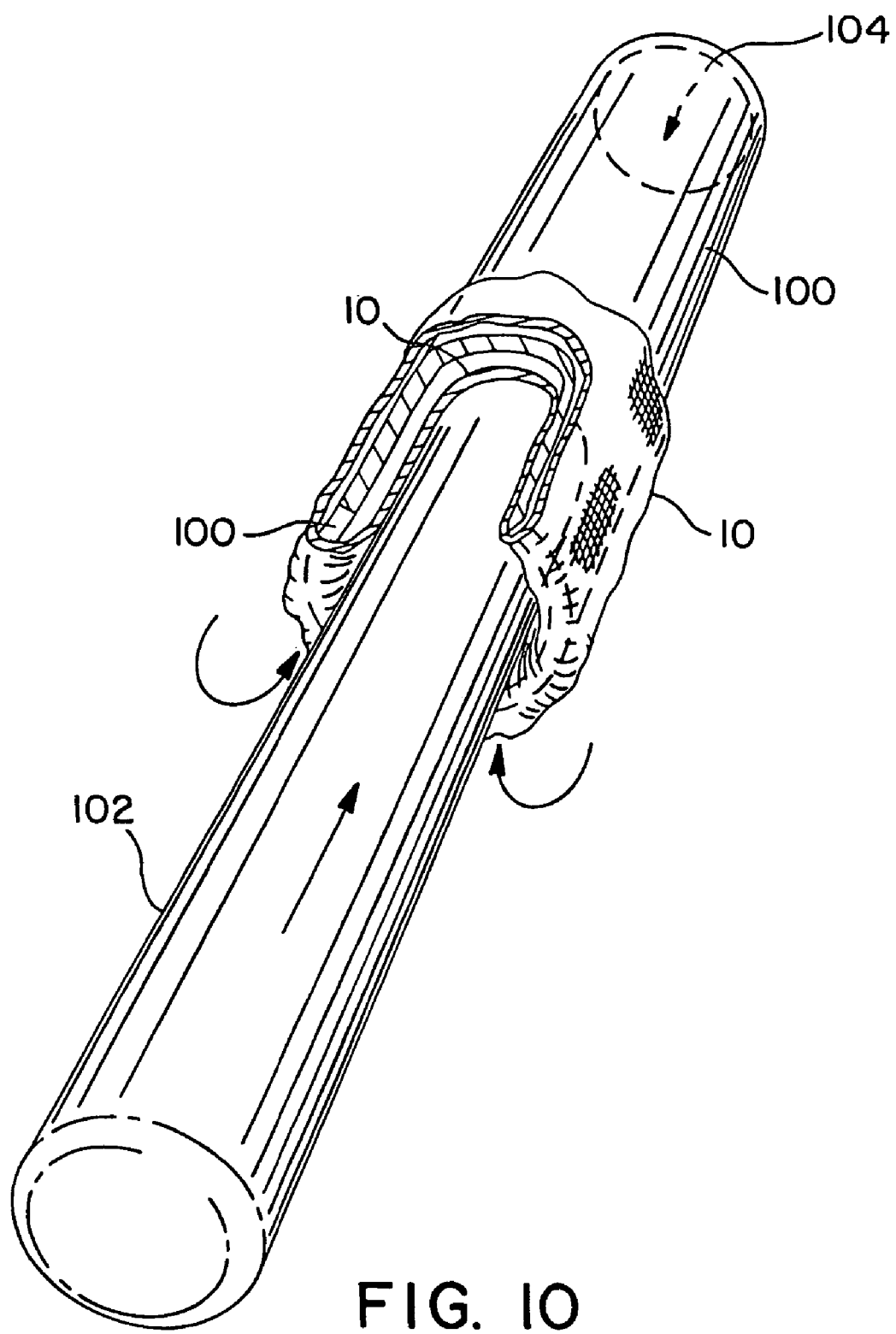
FIG. 10 is a perspective view with cut away portions illustrating one embodiment of a method for turning a dental wipe of the present invention inside-out.

Various methods can be used in order to place the dental wipe in the inside-out position. For instance, the dental wipe can be turned inside-out using a pressurized gas, a vacuum, or mechanical means. For example, one mechanical method for inverting the dental wipe is illustrated in FIG. 10. As shown, in this embodiment, the dental wipe 10 is placed over a cylinder 100. The cylinder 100 defines a passage 104. In order to invert the dental wipe 10, a rod 102, preferably with a compressible tip, is used to push against the closed end of the dental wipe until the dental wipe is pushed all the way through the passage 104. Through this process, the dental wipe 10 is inverted.

As shown in FIGS. 1–4, the first section 20 can also, in some embodiments, have a length greater than the second section 30 such that the first section 20 includes a portion (or pull-on tab) 26 that extends beyond the edge of the second section 30. By extending beyond the second section 30, the portion 26 can facilitate placement of the dental wipe 10 over a finger. In particular, a user can conveniently grab the portion 26 to place the dental wipe 10 over a finger. Besides the first section 20, a pull-on tab can be positioned on any suitable portion of the dental wipe. For instance, the pull-on tab can be located on the second section also.

Further, in another embodiment, the pull-on tab 26 can also be provided in the middle portion of the dental wipe 10 such that a user can is pull the pull-on tab 26 in a direction perpendicular to the lengthwise direction of a flattened dental wipe as shown in phantom in FIG. 4. As a result, the pull-on tab 26 can facilitate the insertion of a finger into the wipe 10 by "spreading out" the sleeve in an upwardly direction as a finger is inserted therein.

Figure 9:
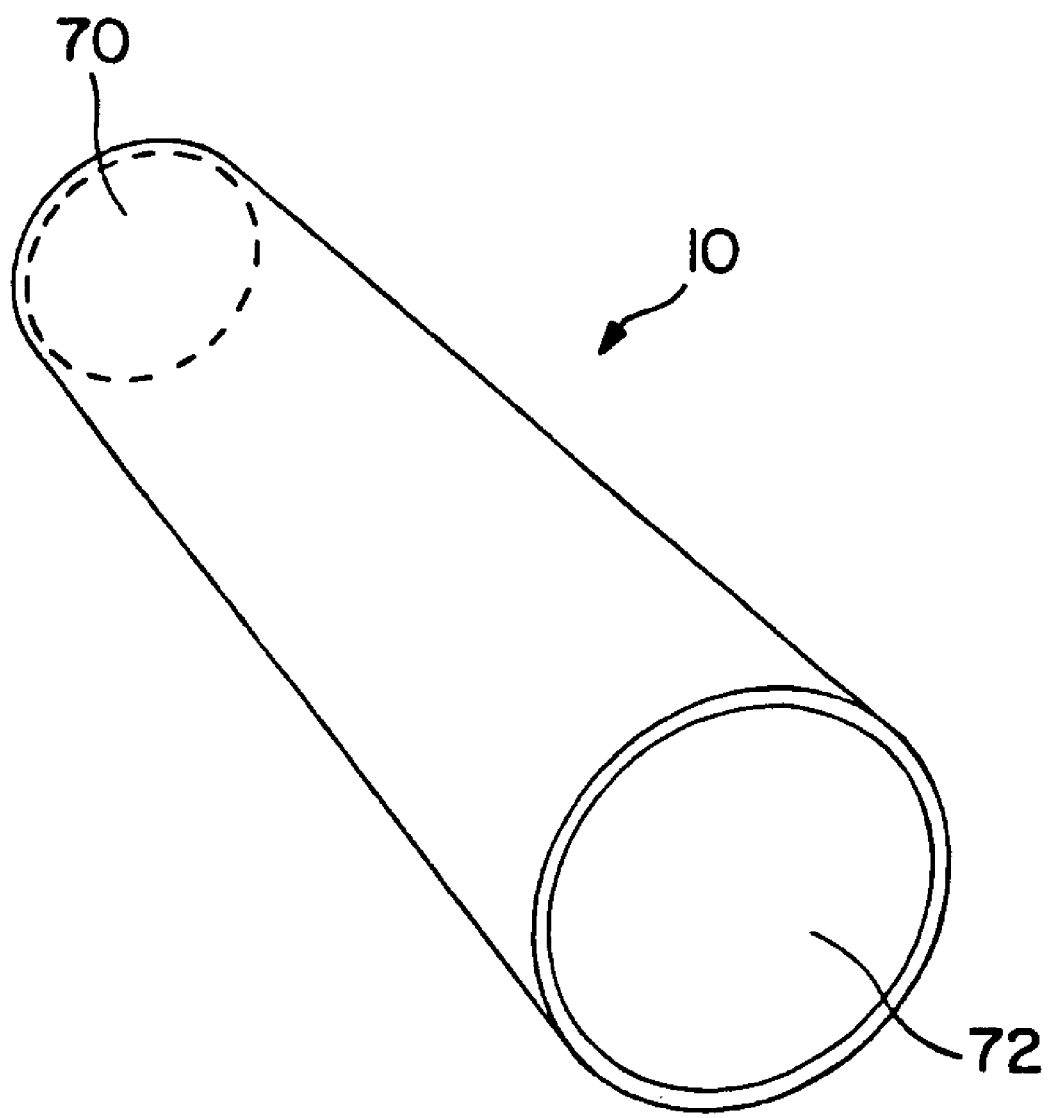
FIG. 9 is a perspective view of a tapered dental wipe having two open ends according to one embodiment of the present invention.

Moreover, although not specifically shown, a dental wipe of the present invention can include bristles on the first section 20 and/or the second section 30. For example, bristles such as described in U.S. Pat. No. 4,617,694 to Bori or U.S. Pat. No. 5,287,584 to Skinner, which are incorporated herein by reference, can be utilized with a dental wipe of the present invention. Further, in other embodiments, as shown in FIG. 9, a dental wipe 10 can also be provided with a tapered shape to enhance the ability of the wipe to fit onto a finger. In addition, as shown in FIG. 9, a dental wipe 10 can have two open ends 70 & 72 so that a finger can be inserted completely therethrough.

In some embodiments of the present invention, it may also be desirable to provide a dental wipe 10 with an additional fastening means. In addition to or alternative to an elastic component, the dental wipe can include a fastening mechanism which can attach to one finger of a user, while the dental wipe itself is fitted onto another finger. Besides being attached to a finger, however, it should be understood that the fastening mechanism can also be designed to be attached to a wrist or some other structure or body part. For example, as shown in FIG. 7, one embodiment of a fastening mechanism of the present invention includes a fastening portion that can fit around a finger of a user.

Figure 7:
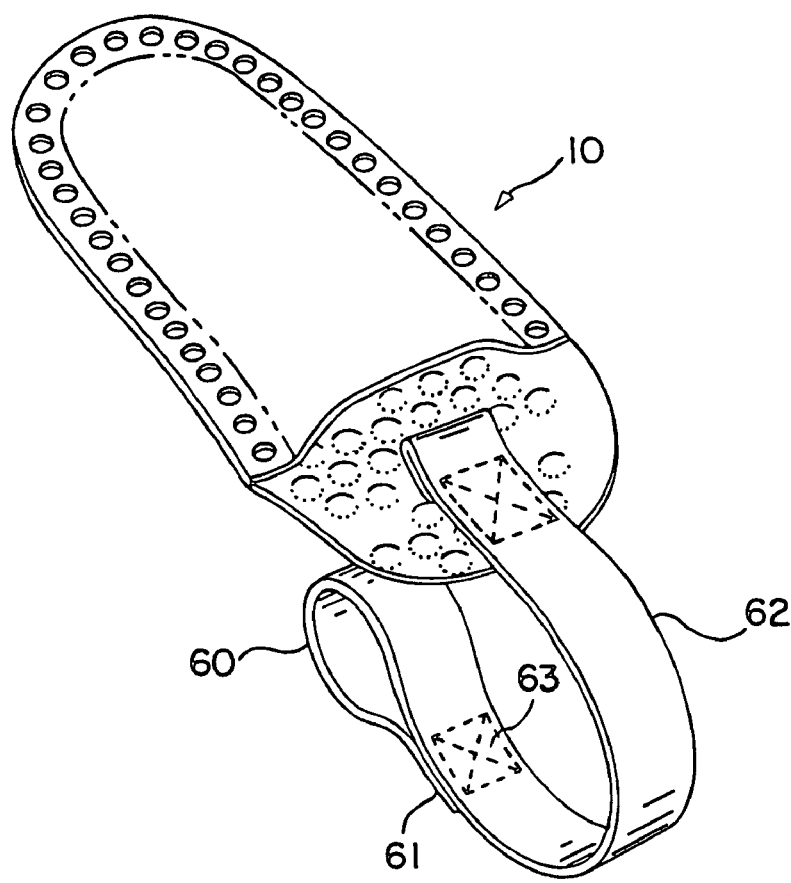
FIG. 7 is a perspective view of a dental wipe having a fastening mechanism according to one embodiment of the present invention.

In one embodiment of the present invention, as shown in FIG. 7, the fastening mechanism can also include a linking portion 62 for attaching the fastening portion 60 to the dental wipe 10. When utilized, the linking portion 62 can be attached to the wipe using a variety of well known attachment methods, such as thermal, chemical, or mechanical bonding. For example, in one embodiment, the linking portion 62 is attached to the dental wipe 10 by an adhesive. In another embodiment, as shown in FIG. 7, a linking portion 62 is attached to a wipe 10 by stitching. Alternatively, the linking portion 62 can be integral with the dental wipe.

In general, the linking portion 62 can be made from a variety of materials, such as strings, bands, cords, fibers, strands, dental floss nonwovens, etc. For most applications, the linking portion 62 can have a length of from about 1 inch to about 12 inches.

In general, the fastening portion 60 can have any shape. For instance, in the embodiment shown in FIG. 7, the fastening portion 60 is formed to have a loop or ring shape so that it can be secured on a finger. Moreover, the fastening portion can also be formed into a certain shape from the linking portion itself. For instance, as shown in FIG. 7, an end 61 of the linking portion 62 is folded and attached to a portion 63 of the linking portion 62 via stitching to form a ring-shaped fastening portion 60. It should be understood that the end 61 can also be attached to the portion 63 by any attachment method known in the art, such as, for example, thermal, chemical, or mechanical bonding methods. Although not specifically depicted, a fastening portion 60 can also be formed from a material separate from the linking portion 62. When formed separately, the fastening portion 60 can be attached to the linking portion 60 by any attachment method known in the art, such as, for example, thermal, chemical, or mechanical bonding methods.

Typically, the fastening portion can be made from the same or a different material than the linking portion. For example, in one embodiment, a fastening portion 60 is made from an elastic material, such as an elastomeric nonwoven, which can allow the fastening portion to fit more tightly around a finger.

In general, the dental wipe of the present invention, such as depicted in FIGS. 1–9, can be formed from variety of materials. For instance, as stated above, in one embodiment, the dental wipe can be formed as a unitary structure from a base web. In another embodiment, the dental wipe can be formed from two sections made from the same or different base webs. It should be understood, however, that, as used herein, a base web of the present invention is meant to include one or more layers of fibrous materials. Generally, a base web of the present invention can contain any material used in the art for making wipes.

For most applications, dental wipes made in accordance with the present invention are constructed from nonwoven webs containing an elastic component referred to herein as an "elastic nonwoven". An elastic nonwoven is a nonwoven material having nonelastic and elastic components or having purely elastic components.

The elastic component can form a separate section of the dental wipe. For example, the dental wipe can be made from two or more sections of material that includes a first section made from a non-elastic material and a second section made from an elastic material. The non-elastic material can be used to clean the teeth, gums and tongue of the user, while the elastic material can be used to ensure that the dental wipe fits snugly over the finger of the user. In one embodiment, the non-elastic material can be texturized for cleaning the teeth, gums and tongue, while the elastic material can have a smooth surface for use in polishing the teeth, gums and tongue of the user.

Alternatively, the dental wipe can be made from a single piece of an elastic nonwoven. The elastic component contained in the elastic nonwoven can be a film, strands, a nonwoven web or elastic filaments incorporated into a laminate structure that is well suited to cleaning or scrubbing one's teeth.

Non-elastic materials used in the present invention typically include nonwoven webs or films. The nonwoven webs, for instance, can be meltblown webs, spunbond webs, carded webs, and the like. The webs can be made from various fibers, such as synthetic or natural fibers.

For instance, in one embodiment, synthetic fibers, such as fibers made from thermoplastic polymers, can be used to construct the dental wipe of the present invention. For example, suitable fibers could include melt-spun filaments, staple fibers, melt-spun multi-component filaments, and the like.

The synthetic fibers or filaments used in making the nonwoven material of the base web may have any suitable morphology and may include hollow or solid, straight or crimped, single component, conjugate or biconstituent fibers or filaments, and blends or mixtures of such fibers and/or filaments, as are well known in the art.

The synthetic fibers used in the present invention may be formed from a variety of thermoplastic polymers where the term "thermoplastic polymer" refers to a long chain polymer that repeatedly softens when exposed to heat and substantially returns to its original state when cooled to ambient temperature. As used herein, the term "polymer" generally includes, but is not limited to, homopolymers, copolymers, such as for example, block, graft, random, and alternating copolymers, terpolymers, etc., and blends and modifications thereof. As used herein, the term "blend" means a mixture of two or more polymers. Furthermore, unless otherwise specifically limited, the term "polymer" shall include all possible geometrical configurations of the molecule. These configurations include, but are not limited to, isotactic, synditactic, and random symmetries.

Exemplary thermoplastics include, without limitation, poly(vinyl) chlorides, polyesters, polyamides, polyfluorocarbons, polyolefins, polyurethanes, polystyrenes, poly(vinyl) alcohols, caprolactams, and copolymers of the foregoing, and elastomeric polymers such as elastic polyolefins, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene), A-B-A-B tetrablock copolymers and the like.

Many polyolefins are available for fiber production, for example polyethylenes such as Dow Chemical's PE XU 61800.41 linear low density polyethylene ("LLDPE") and 25355 and 12350 high density polyethylene ("HDPE") are such suitable polymers. Fiber-forming polypropylenes include Exxon Chemical Company's Escorene7 PD 3445 polypropylene and Montell Chemical Co.'s PF-304 and PF-015. Many other polyolefins are commercially available and include polybutylenes and others.

Examples of polyamides and their methods of synthesis may be found in "Polymer Resins" by Don E. Floyd (Library of Congress Catalog No. 66-20811, Reinhold Publishing, New York, 1966). Particularly commercially useful polyamides are nylon-6, nylon 6,6, nylon-11 and nylon-12. These polyamides are available from a number of sources such as Emser Industries of Sumter, South Carolina (Grilon7 & Grilamid7 nylons), "tochem Inc. Polymers Division of Glen Rock, N.J. (Rilsan7 nylons), Nyltech of Manchester, N.H. (grade 2169, Nylon 6), and Custom Resins of Henderson, Ky. (Nylene 401-D), among others.

As stated above, synthetic fibers added to the base web can also include staple fibers which can be added to increase the strength, bulk, softness and smoothness of-the base sheet. Staple fibers can include, for instance, various polyolefin fibers, polyester fibers, nylon fibers, polyvinyl acetate fibers, cotton fibers, rayon fibers, non-woody plant fibers, and mixtures thereof. In general, staple fibers are typically longer than pulp fibers. Staple fibers can increase the strength and softness of the final product.

The fibers used in the base web of the present invention can also be curled or crimped. The fibers can be curled or crimped, for instance, by adding a chemical agent to the fibers or subjecting the fibers to a mechanical process. Curled or crimped fibers may create more entanglement and void volume within the web and further increase the amount of fibers oriented in the z-direction as well as increase web strength properties. As used herein, the z-direction refers to the direction perpendicular to the length and width of the base web.

The synthetic fibers added to the base web can also include bicomponent fibers. Bicomponent fibers are fibers that can contain two materials such as but not limited to in a side by side arrangement, in a matrix-fibril arrangement wherein a core polymer has a complex cross-sectional shape, or in a core and sheath arrangement. In a core and sheath fiber, generally the sheath polymer has a lower melting temperature than the core polymer to facilitate thermal bonding of the fibers. For instance, the core polymer, in one embodiment, can be nylon or a polyester, while the sheath polymer can be a polyolefin such as polyethylene or polypropylene. Such commercially available bicomponent fibers include "CELBOND" fibers marketed by the Hoechst Celanese Company.

Besides or in addition to synthetic fibers, pulp fibers can also be used to construct the dental wipe of the present invention. The pulp fibers used in forming the base web may be softwood fibers having an average fiber length of greater than 1 mm, and particularly from about 2 to 5 mm based on a length-weighted average. Such fibers can include Northern softwood kraft fibers, redwood fibers and pine fibers. Secondary fibers obtained from recycled materials may also be used. In addition, hardwood pulp fibers, such as eucalyptus fibers, can also be utilized in the present invention.

Besides the above-mentioned fibers, thermomechanical pulp fibers can also be added to the base web. Thermomechanical pulp, as is known to one skilled in the art, refers to pulp that is typically cooked during the pulping process to a lesser extent than conventional pulps. Thermomechanical pulp tends to contain stiff fibers and has higher levels of lignin. Thermomechanical pulp can be added to the base web of the present invention in order to create an open pore structure, thus increasing bulk and absorbency and improving resistance to wet collapse.

When present, thermomechanical pulp can be added to a layer of the base web in an amount from about 10% to about 30% by weight of the fibers contained in the layer. When using thermomechanical pulp, a wetting agent may be added during formation of the web. The wetting agent can be added in an amount less than about 1% by weight of the fibers. In general, any suitable wetting agent can be used in the present invention. For example, in one embodiment, the wetting agent can be a sulphonated glycol.

When pulp fibers are used to form the base web, the web can be treated with a chemical debonding agent to reduce inner fiber-to-fiber strength. Suitable debonding agents that may be used in the present invention when the base web contains pulp fibers include cationic debonding agents such as fatty dialkyl quaternary amine salts, mono fatty alkyl tertiary amine salts, primary amine salts, imidazoline quaternary salts, and unsaturated fatty alkyl amine salts. Other suitable debonding agents are disclosed in U.S. Pat. No. 5,529,665 to Kaun, which is incorporated herein by reference. In one embodiment, the debonding agent can be an organic quaternary ammonium chloride. In this embodiment, the debonding agent can be added to the fiber furnish in an amount from about 0.1% to about 1% by weight, based on the total weight of fibers present within the furnish.

Moreover, in some embodiments of the present invention, the base web of the present invention can also be hydraulically entangled (or hydroentangled) to provide further strength. Hydroentangled webs, which are also known as spunlace webs, refer to webs that have been subjected to columnar jets of a fluid that cause the fibers in the web to entangle. Hydroentangling a web typically increases the strength of the web. Thus, according to the present invention, in order to increase the strength of a web, the base web of the present invention can be hydroentangled. For example, in one embodiment, the base web can comprise HYDROKNIT7, a nonwoven composite fabric that contains 70% by weight pulp fibers that are hydraulically entangled into a continuous filament material. HYDROKNIT7 material is commercially available from Kimberly-Clark Corporation of Neenah, Wis. Hydraulic entangling may be accomplished utilizing conventional hydraulic entangling equipment such as may be found in, for example, in U.S. Pat. No. 3,485,706 to Evans or U.S. Pat. No. 5,389,202 to Everhart et al., the disclosures of which are hereby incorporated by reference.

As mentioned above, for most applications, nonwoven webs used to construct the dental wipe will contain synthetic fibers. For nonwoven webs containing substantial amounts of synthetic fibers, the webs may be bonded or otherwise consolidated in order to improve the strength of the web. Various methods may be utilized in bonding webs of the present invention. Such methods include through-air bonding and thermal point bonding as described in U.S. Pat. No. 3,855,046 to Hansen et al, which is incorporated herein by reference. In addition, other conventional means of bonding, such as oven bonding, ultrasonic bonding, hydroentangling, or combinations of such techniques, may be utilized in certain instances.

In one embodiment, thermal point bonding is used which bonds the fibers together according to a pattern. In general, the bonding areas for thermal point bonding, whether pattern unbonded or pattern bonded fabrics, can be in the range of 50% total bond area or less. More specifically, the bond areas of the present inventive webs can be in the range of about 40% total bond area or less. Even more specifically, the bond areas can be in the range of about 30% total bond area or less and may be in the range of about 15% total bond area or less. Typically, a bond area of at least about 10% can be acceptable for creating the base webs of the present invention, although other total bond areas will fall within the scope of the invention, depending on the particular characteristics desired in the final product. Stated generally, the lower limit on the percent bond area suitable for forming the nonwoven material of the present invention is the point at which fiber pull-out reduces the surface integrity and durability of the material. The percent bond areas will be affected by a number of factors, including the type(s) of polymeric materials used in forming the fibers or filaments of the nonwoven web, whether the nonwoven web is a single- or multi-layer fibrous structure, and the like. Bond areas ranging from about 15% to about 50%, and more particularly from about 15% to about 40%, have been found suitable.

Base webs constructed for use in the dental wipe of the present invention desirably include a texturized surface where the dental wipe is to contact a user's teeth and gums. The texturized surface can facilitate removal of residue and film from the teeth and gums. The texturized surface can be positioned on the dental wipe only where the dental wipe is to contact the teeth and gums or can completely cover the exterior surface of the dental wipe. In this regard, referring to FIG. 3, one embodiment of the present invention includes a second section 30 that is made from a base web comprising a nonwoven texturized material. In particular, when the dental wipe 10 is placed onto a finger, as shown in FIG. 1, the second section 30 can be used in order to clean and/or massage the teeth or gums of the desired subject.

The manner in which a texturized surface is formed on a nonwoven web for use in the present invention can vary depending upon the particular application and the desired result. In the embodiment shown in FIG. 3, the second section 30 is made from a nonwoven web that has been thermally point unbonded to form a plurality of tufts 31. As used herein, a substrate that has been "thermally point unbonded" refers to a substrate that includes raised unbonded areas or lightly bonded areas that are surrounded by bonded regions. For example, as shown in FIG. 3, the tufts 31 are the unbonded or lightly bonded areas that form raised projections off the surface of the nonwoven web to provide the necessary texture.

It is believed that the thermally point unbonded abrasive surfaces made according to the present invention are unique and provide various advantages and benefits not only when used in dental wipe applications, but also when used in other applications. For instance, referring to FIG. 14, a point unbonded material generally 76 made according to the present invention is shown. Besides being used to construct dental wipes, it is believed that this material can also be used as an abrasive material in various applications, including use in sanding or polishing products, washcloths, brushes, etc. Such materials are defined by having semi-rigid protuberances of a certain height, particularly having a height of greater than about 0.02 inches.

Figure 14:
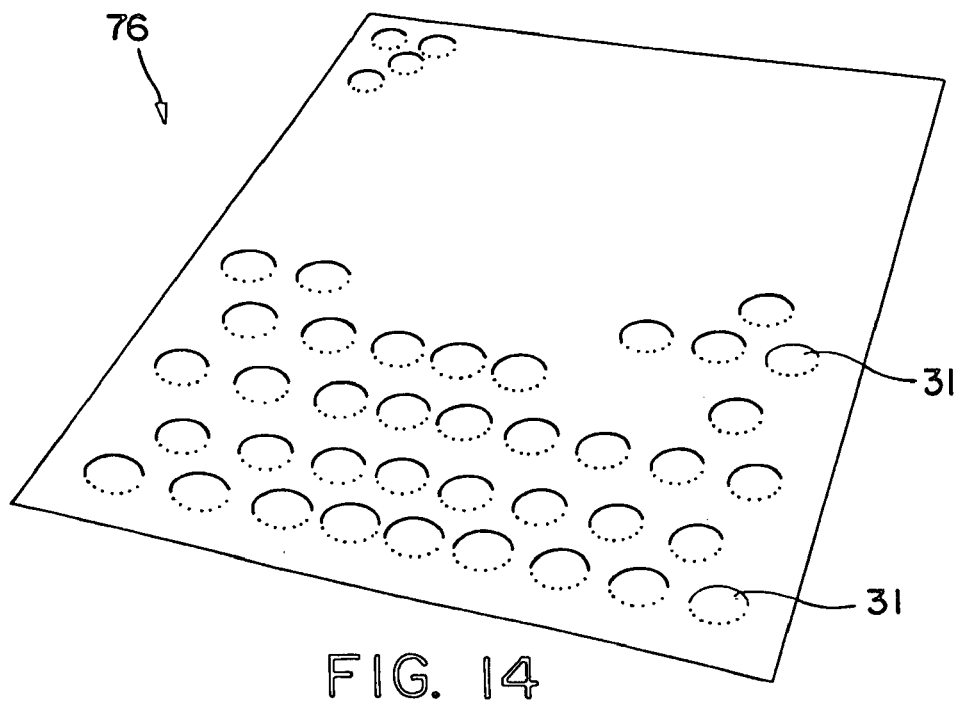
FIG. 14 is a perspective view of a texturized material for use in the present invention.

In the past, various point unbonded products have been made. For instance, a point unbonded material is commonly used as the loop material for a hook and loop fastener. Materials made in the past, however, have not been made with protuberances or tufts 31 as shown in FIG. 14 with the height of the present invention. The present inventors have discovered not only a new process for producing point unbonded materials, but also a new product having improved abrasive properties.

Figure 15:
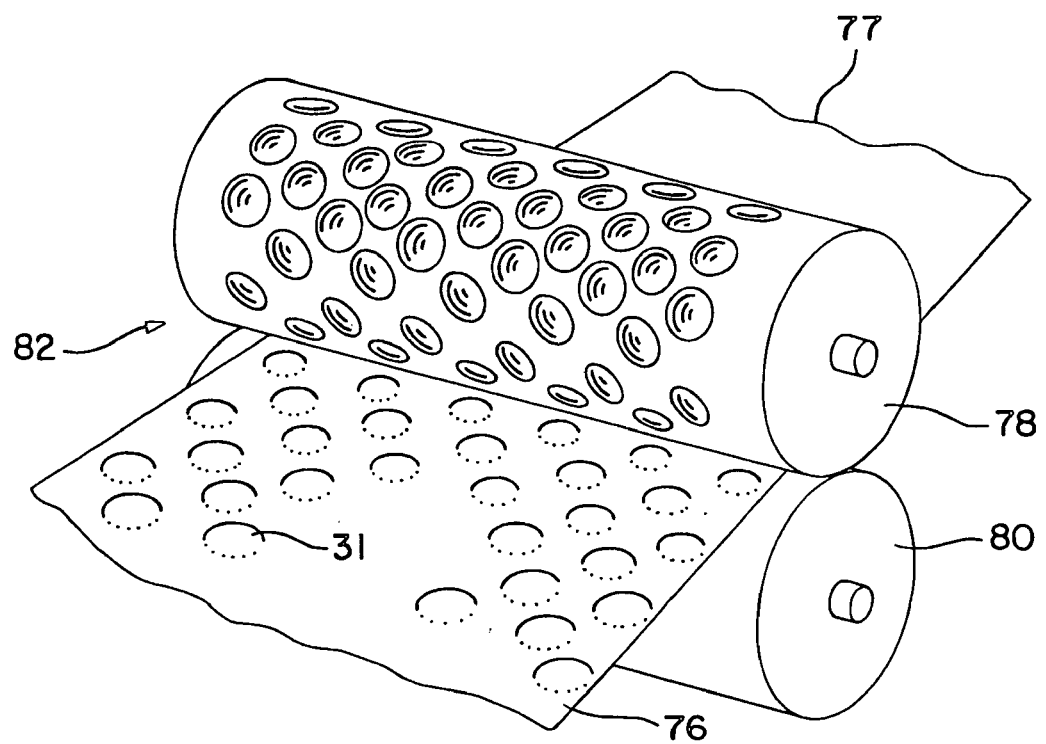
FIG. 15 is a perspective view of one embodiment of a process for producing the material illustrated in FIG. 14.

Referring to FIG. 15, one embodiment of a process for producing the point unbonded material 76 is illustrated. As shown, a nonwoven substrate 77 is fed into a nip generally 82 formed between a first patterned roll 78 and a second smooth roll 80. Once the substrate is fed through the nip 82, the tufts 31 are formed. As shown, the tufts 31 are surrounded by bonded, compressed regions.

The substrate 77 used to produce the point unbonded material 76 can vary depending upon the particular application. For instance, the substrate 77 can be a single layer or can include multiple layers of material. For most applications, the total basis weight of the substrate 77 should be at least 3 osy, and particularly from about 3 osy to about 9 osy. Higher basis weights are needed in order to produce tufts 31 with an appropriate height.

For most applications, the substrate 77 should also include at least one nonwoven layer that has a high bulk to mass ratio. Examples of materials having high bulk include through air bonded nonwoven webs made from polymeric fibers and filaments. The nonwoven webs can be made from crimped polymeric fibers and filaments and/or from fibers and filaments having a shaped cross-sectional profile. For example, crimped bicomponent polyethylene/polypropylene fibers can be used or mechanically crimped polypropylene fibers can be used. Shaped fibers include pentalobal fibers and hollow fibers.

Besides nonwovens having high bulk, the substrate 77 can also include films. For example, in one embodiment, a nonwoven web can be combined with a moisture barrier film in producing the point unbonded material 76.

As shown in FIG. 15, once the appropriate substrate 77 is chosen, the substrate is fed through the nip 82. In one embodiment, the point unbonded material 76 is formed through a thermal bonding process. For instance, in one embodiment, the patterned roll 78 and/or the smooth roll 80 can be heated to a temperature sufficient to melt and fuse the substrate 77 in the areas between the tufts 31. The temperature to which the rolls 78 and 80 are heated depends upon the particular application, and particularly on the materials that are used to form the substrate 77. The temperature to which the rolls is heated is also dependent upon the amount of pressure applied to the substrate 77.

In one embodiment, when processing substrates containing polyolefin fibers, the rolls can be heated to a temperature of from about 230° F. to about 280° F., and particularly from about 240° F. to about 260° F. For most applications, both rolls 78 and 80 are heated. Patterned roll 78, however, can be heated to a higher temperature than roll 80 and vice versa.

When producing the point unbonded material 76, the speed of the substrate entering the nip, the amount of tension placed upon the substrate and the pressure within the nip are all important factors that need to be optimized in producing the product. For instance, the speed at which the substrate is fed through the nip 82 can vary from about 5 feet per minute to about 100 feet per minute when using conventionally sized rolls.

Besides thermal bonding, ultrasonic bonding can also be used to produce the point unbonded material 76. Ultrasonic bonding can be carried out using a stationary device (not shown) or a rotary device as shown in FIG. 15. During ultrasonic bonding, patterned roll 78 is vibrated which causes the tufts 31 to form. The present inventors have determined that ultrasonic bonding operates more efficiently than thermal bonding. It has also been determined that ultrasonic bonding is capable of processing thicker and heavier substrates than thermal bonding. For example, ultrasonic bonding can process substrates having a basis weight up to 9 osy. Conventional thermal bonding systems, however, are better suited for processing substrates having a basis weight up to about 5 osy. Ultrasonic bonding also produces subtle differences in the morphological characteristics of the surface in comparison to conventional thermal bonding.

As described above, the point unbonded material 76 contains tufts having a height of at least 0.02 inches. More particularly, the height of the tufts will vary from about 0.05 inches to about 0.1 inches. As shown in FIG. 15, the tufts can have a circular shape. It should be understood, however, that tufts 31 can have any suitable shape. For instance, the tufts can be square, triangular, or even in the shape of a doughnut.

The total bond area surrounding the tufts 31 can also vary depending upon the particular application. For most embodiments, the bond area surrounding the tufts can be from about 15% to about 40% of the surface area of the material, and particularly from about 20% to about 40% of the surface area of the material.

In one particular embodiment of the present invention, the point unbonded material 76 is made from two substrate layers. The first substrate layer is a through air bonded web having a basis weight of 3.25 osy. The web can be made from crimped bicomponent polypropylene/polyethylene fibers. The second substrate, on the other hand, is a through air bonded nonwoven web made from shaped pentalobal fibers. The second web can also have a basis weight of about 3.25 osy. Both webs can be fed simultaneously into the nip 82 and subjected to ultrasonic bonding to produce tufts 31.

In another alternative embodiment of the present invention, the point unbonded material 76 is made from a breathable stretched polyethylene film sandwiched between a through air bonded nonwoven web having a basis weight of about 3.5 osy and a second spunbond web having a basis weight of about 0.5 osy. The first nonwoven web can be made from crimped bicomponent fibers, while the spunbond web can be made from polypropylene filaments.

It should be understood, however, that the materials and conditions used to make the point unbonded material 76 can vary depending upon the ultimate application of the material.

Besides point unbonded materials, there are many other methods for creating texturized surfaces on base webs and many other texturized materials can be utilized.

Examples of known nonwoven, texturized materials, include rush transfer materials, flocked materials, wireform nonwovens, and the like. Moreover, through-air bonded fibers, such as through-air bonded bicomponent spunbond, can be incorporated into the base web to provide texture to the wipe.

Texturized webs having projections from about 0.1 mm to about 25 mm, such as pinform meltblown or wireform meltblown, can also be utilized in the base web of the present invention. Still another example of suitable materials for a texturized base web include texturized coform materials. In general, "coform" means a process in which at least one meltblown in die is arranged near a chute through which other materials are added to the web while it forms. Such other materials can include, for example, pulp, superabsorbent particles, or cellulose or staple fibers. Coform processes are described in U.S. Pat. No. 4,818,464 to Lau and U.S. Pat. No. 4,100,324 to Anderson et al., which are incorporated by reference. Webs produced by the coform process are generally referred to as coform materials.

In one embodiment, the texturized material can be a loop material. As used herein, a loop material refers to a material that has a surface that is at least partially covered by looped bristles. It is believed that looped bristles provide various advantages in relation to conventional bristles. For example, the inherent stiffness in a looped structure allows the use of finer yarns and a corresponding increase in surface area for a given stiffness. The lack of a sharp end on a looped bristle may reduce abrasion, which refers to the damage that can occur to soft tissue in the mouth.

The looped bristles that can be used in the present invention can vary depending upon the particular application. For instance, the stiffness of the looped bristles can be varied by varying different factors, including the height of the loop, the inherent properties of the looped material, the fiber diameter, the fiber type, and any post-formation treatments (e.g. chemical coatings) that may be performed on the looped material.

In general, the height of the looped bristles should be short enough so that the loops are unlikely to get snagged on teeth or dental work, but still sufficiently long to be effective in cleaning the interproximal areas of the teeth. For most applications, the loops should be less than about 20 mm, particularly from about 1 mm to about 5 mm, and more particularly from about 1.5 mm to about 3.5 mm. The height of the looped bristles on a loop material can be homogenous or heterogenous. The looped bristles can be contained on the looped material according to a particular pattern or can be randomly arranged on the loop material. For example, in one embodiment, the looped bristles can be arranged in rows and columns on the loop material. The looped bristles can be arranged vertically or at any suitable angle to the surface of the material. Further, the looped bristles can be sparsely spaced apart or can be densely packed together.

The loop material can be made in a number of different ways. For example, the loop can be a woven fabric or a knitted fabric. In one embodiment, the loop material is made by needle punching loops into a substrate. In other embodiments, the loop material can be formed through a hydroentangling process or can be molded, such as through an injection molding process. Of course, any other suitable technique known in the art for producing looped bristles can also be used.

The looped bristles can be made from various natural or synthetic materials. For instance, the bristles can be made from polyester, nylon, polypropylene, polyethylene, polylactic acid, or various other polymers. The looped bristles can also be made from natural fibers, including cotton or wool. The looped bristles can be made from monofilament yarns, multi-filament yarns, or spun yarns.

Further, the yarns can be shaped filaments, such as a multi-lobal shaped filament. As used herein "shaped" filaments or fibers refer to filaments or fibers not having a circular cross sectional shape. For example, a pentalobal filament can be used.

In accordance with the present invention, the looped bristles can be flavored or unflavored. Further, the looped bristles can be treated, such as with a fluoride compound or other additive described herein, or untreated.

Further, the looped bristles can be made from the same material as the base material on which the bristles are contained or can be made from a different material. For example, as described above, the bristles can be needle punched into a woven or non-woven backing layer. The loop material can also be made from a single layer of material or can be a laminate. For example, a base layer containing the looped bristles can be laminated to various other layers. For example, the base layer can be laminated to a woven layer, a knitted layer, a non-woven layer, an expandable layer such as spandex, a stretch bonded layer, or a neck bonded layer, or can be attached to various non-woven webs including spunbonded webs or spunbond-meltblown-spunbond laminate.

In order to alter the characteristics of the loop material, various post processing steps can also be performed in the material. For example, the material can undergo a shearing process, a napping process, a cleaning process, or a sanding process. During these processes some of the loops can be abraded and/or cut. For example, in one embodiment, a portion of the loops can be sheared. In another embodiment, these processing steps can be used not to cut the loops, but to fray the loops for making the bristles softer.

In one particular embodiment of the present invention, the loop material used in the dental wipe is a loop material commonly used in hook and loop fasteners. For example, VELCRO loops No. 002 made by VELCRO, USA, Inc. can be used. This material is made with nylon loops. In an alternative embodiment, the looped fastener material can be elastic. Elastic woven loop materials include VEL-STRETCH Tape 9999 and MEDFLEX Tape 9399, both marketed by VELCRO, USA, Inc.

As described above, besides containing various non-elastic materials and, if desired, a texturized surface, the dental wipe of the present invention can also contain an elastomeric component.

By containing such an elastomeric component, the dental wipe of the present invention can better fit around a human finger. In this regard, referring to FIG. 8, one embodiment of the present invention is depicted that includes a dental wipe made from a base web having at least one elastomeric component. In particular, the dental wipe 10 can be formed into a unitary structure from a base web that includes an elastomeric material. Moreover, in other embodiments, such as shown in FIG. 2, one section 20 of the dental wipe can include an elastomeric component.

When present in the dental wipe, the elastomeric component can take on various forms. For example, the elastomeric component can be elastic strands or sections uniformly or randomly distributed throughout the base web. Alternatively, the elastomeric component can be an elastic film or an elastic nonwoven web. The elastomeric component can also be a single layer or a multi-layered material.

In general, any material known in the art to possess elastomeric characteristics can be used in the present invention as an elastomeric component. For example, suitable elastomeric resins include block copolymers having the general formula A-B-A' or A-B, where A and A' are each a thermoplastic polymer endblock which contains a styrenic moiety such as a poly(vinyl arene) and where B is an elastomeric polymer midblock such as a conjugated diene or a lower alkene polymer. Block copolymers form the A and A' blocks, and the present block copolymers are intended to embrace linear, branched and radial block copolymers. In this regard, the radial block copolymers may be designated (A-B)$_m$-X, wherein X is a polyfunctional atom or molecule and in which each (A-B)$_m$-radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer," and particularly "A-B-A" and "A-B" block copolymer, is intended to embrace all block copolymers having such rubbery blocks and thermoplastic blocks as discussed above, which can be extruded (e.g., by meltblowing), and without limitation as to the number of blocks. The elastomeric nonwoven web may be formed from, for example, elastomeric (polystyrene/poly (ethylene-butylene)/polystyrene) block copolymers. Commercial examples of such elastomeric copolymers are, for example, those known as KRATON materials which are available from Shell Chemical Company of Houston, Tex. KRATON block copolymers are available in several different formulations, a number of which are identified in U.S. Pat. Nos. 4,663,220, 4,323,534, 4,834,738, 5,093,422 and 5,304,599, which are all hereby incorporated by reference.

Polymers composed of an elastomeric A-B-A-B tetrablock copolymer may also be used in the practice of this invention. Such polymers are discussed in U.S. Pat. No. 5,332,613 to Taylor et al. In such polymers, A is a thermoplastic polymer block and B is an isoprene monomer unit hydrogenated to substantially a poly(ethylene-propylene) monomer unit. An example of such a tetrablock copolymer is a styrene-poly(ethylene-propylene)-styrene-poly(ethylene-propylene) or SEPSEP elastomeric block copolymer available from the Shell Chemical Company of Houston, Tex. under the trade designation KRATON G-1657.

Other exemplary elastomeric materials which may be used include polyurethane elastomeric materials such as, for example, those available under the trademark ESTANE from B.F. Goodrich & Co. or MORTHANE from Morton Thiokol Corp., polyester elastomeric materials such as, for example, those available under the trade designation HYTREL from E.I. DuPont De Nemours & Company, and those known as ARNITEL, formerly available from Akzo Plastics of Amhem, Holland and now available from DSM of Sittard, Holland.

Another suitable material is a polyester block amide copolymer having the formula:

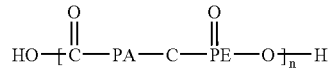

where n is a positive integer, PA represents a polyamide polymer segment and PE represents a polyether polymer segment. In particular, the polyether block amide copolymer has a melting point of from about 150° C. to about 170° C., as measured in accordance with ASTM D-789; a melt index of from about 6 grams per 10 minutes to about 25 grams per 10 minutes, as measured in accordance with ASTM D-1238, condition Q (235 C/1 Kg load); a modulus of elasticity in flexure of from about 20 Mpa to about 200 Mpa, as measured in accordance with ASTM D-790; a tensile strength at break of from about 29 Mpa to about 33 Mpa as measured in accordance with ASTM D-638 and an ultimate elongation at break of from about 500 percent to about 700 percent as measured by ASTM D-638. A particular embodiment of the polyether block amide copolymer has a melting point of about 152° C. as measured in accordance with ASTM D-789; a melt index of about 7 grams per 10 minutes, as measured in accordance with ASTM D-1238, condition Q (235 C/1 Kg load); a modulus of elasticity in flexure of about 29.50 Mpa, as measured in accordance with ASTM D-790; a tensile strength at break of about 29 Mpa, a measured in accordance with ASTM D-639; and an elongation at break of about 650 percent as measured in accordance with ASTM D-638. Such materials are available in various grades under the trade designation PEBAX from ELF Atochem Inc. of Glen Rock, N.J. Examples of the use of such polymers may be found in U.S. Pat. Nos. 4,724,184, 4,820,572 and 4,923,742 to Killian which are incorporated herein by reference.

Elastomeric polymers can also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

The thermoplastic copolyester elastomers include copolyetheresters having the general formula:

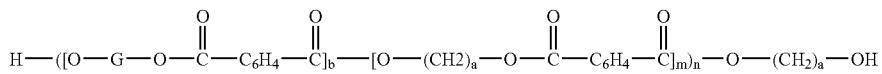

where "G" is selected from the group consisting of poly(oxyethylene)-alpha,omega-diol, poly(oxypropylene)-alpha,omega-diol, poly(oxytetramethylene)-alpha,omega-diol and "a" and "b" are positive integers including 2, 4 and 6, "m" and "n" are positive integers including 1–20. Such materials generally have an elongation at break of from about 600 percent to 750 percent when measured in accordance with ASTM D-638 and a melt point of from about 350° F. to about 400° F. (176 to 205° C.) when measured in accordance with ASTM D-2117.

Commercial examples of such copolyester materials are, for example, those known as ARNITEL, formerly available from Akzo Plastics of Amhem, Holland and now available from DSM of Sittard, Holland, or those known as HYTREL which are available from E.I. DuPont de Nemours of Wilmington, Del. Formation of an elastomeric nonwoven web from polyester elastomeric materials is disclosed in, for example, U.S. Pat. No. 4,741,949 to Morman et al. and U.S. Pat. No. 4,707,398 to Boggs which are herein incorporated by reference.

Elastomeric olefin polymers are available from Exxon Chemical Company of Baytown, Tex. under the trade name ACHIEVE for polypropylene based polymers and EXACT and EXCEED for polyethylene based polymers. Dow Chemical Company of Midland, Mich. has polymers commercially available under the name ENGAGE. These materials are believed to be produced using non-stereoselective metallocene catalysts. Exxon generally refers to their metallocene catalyst technology as "single site" catalysts while Dow refers to theirs as "constrained geometry" catalysts under the name INSIGHT to distinguish them from traditional Ziegler-Natta catalysts which have multiple reaction sites.

When incorporating an elastomeric component, such as described above, into a base web of the present invention, it is often desired that the elastomeric material form an elastic laminate with one or more other layers, such as foams, films, apertured films, and/or nonwoven webs. The elastic laminate generally contains layers that can be bonded together so that at least one of the layers has the characteristics of an elastic polymer. Examples of elastic laminates include, but are not limited to, stretch-bonded laminates and neck-bonded laminates.

The elastic member used in neck bonded materials, stretch-bonded materials, stretch-bonded laminates, neck-bonded laminates and in other similar laminates can be made from materials, such as described above, that are formed into films, such as a microporous film, fibrous webs, such as a web made from meltblown fibers, or foams. A film, for example, can be formed by extruding an elastomeric polymer containing a filler, such as calcium carbonate, and subsequently stretching it to render it microporous.

Fibrous elastic webs can also be formed from an extruded polymer. For instance, as stated above, in one embodiment the fibrous web can contain meltblown fibers. The fibers can be continuous or discontinuous. Meltblown fabrics have been conventionally made by extruding a thermoplastic polymeric material through a die to form fibers. As the molten polymer fibers exit the die, a high pressure fluid, such as heated air or steam, attenuates the molten polymer filaments to form fine fibers. Surrounding cool air is induced into the hot air stream to cool and solidify the fibers. The fibers are then randomly deposited onto a foraminous surface to form a web. The web has integrity but may be additionally bonded if desired.

Besides meltblown webs, however, it should be understood that other fibrous webs can be used in accordance with the present invention. For instance, in an alternative embodiment, elastic spunbond webs can also be formed from spunbond fibers. Spunbond webs are typically produced by heating a thermoplastic polymeric resin to at least its softening temperature, then extruding it through a spinnerette to form continuous fibers, which can be subsequently fed through a fiber draw unit. From the fiber draw unit, the fibers are spread onto a foraminous surface where they are formed into a web and then bonded such as by chemical, thermal or ultrasonic means.

In one embodiment, the elastic member can be a necked stretch bonded laminate. As used herein, a necked stretch bonded laminate is defined as a laminate made from the combination of a neck bonded laminate and a stretch bonded laminate. Examples of necked stretch bonded laminates are disclosed in U.S. Pat. Nos. 5,114,781 and 5,116,662 which are both incorporated herein by reference. Of particular advantage, a necked stretch bonded laminate is stretchable in the machine direction and in the cross machine direction. Further, a necked stretch bonded laminate can be made with a nonwoven facing that is texturized. In particular, the necked stretch bonded laminate can be made so as to include a nonwoven facing that gathers and becomes bunched so as to form a texturized surface. In this manner, the necked stretch bonded laminate can be used to form the entire dental wipe having stretch characteristics in two directions and having a texturized surface for cleaning the teeth and gums of a user.

Besides including a non-elastic component or an elastic component, the dental wipe of the present invention can further include a moisture barrier that is incorporated into or laminated to the base web of the present invention. Such a barrier can prevent, or at least minimize, leakage from outside the wipe by establishing a barrier to the passage of liquid from the wipe to the finger placed therein. For example, as shown in FIG. 4, a layer of material or film can be provided to form the moisture barrier 50, which can act as a barrier between the outer layer of a wipe 10 and a finger. Moreover, in this embodiment, the moisture barrier 50 can act as an inner lining for the second section 30 only, while the first section 20 possesses no such inner lining. However, it should also be understood that the moisture barrier 50 may be a liner for both the first section 20 and the second section 30. It should be understood that the moisture barrier 50 can be applied to the wipe 10 as a layer of the base web, or as an outer lining for the base web. Moreover, it should also be understood that the moisture barrier can be inherent within the base web structure such that it would not constitute a separate lining thereof.

In one particular application, the moisture barrier layer can be used to secure the bristles to a base web. For example, in one embodiment, bristles or looped bristles can be needle punched into a base web. According to this process, holes may form in the base web that would allow liquids to pass from the surface of the dental wipe to the interior of the dental wipe. In this application, the moisture barrier layer can be applied as an inner lining to the base web for not only making the base web liquid impervious, but for also securing the bristles to the surface of the base web.

In one embodiment of the present invention, the moisture barrier 50 can be made from liquid-impermeable plastic films, such as polyethylene and polypropylene films. Generally, such plastic films are impermeable to gases and water vapor, as well as liquids.

While completely liquid-impermeable films can prevent the migration of liquid from outside the wipe to the finger, the use of such liquid- and vapor-impermeable barriers can sometimes result in a relatively uncomfortable level of humidity being maintained in a wipe 10.

As such, in some embodiments, breathable, liquid-impermeable barriers are desired. For instance some suitable breathable, liquid-impermeable barriers can include barriers such as disclosed in U.S. Pat. No. 4,828,556 to Braun et al., which is incorporated herein in its entirety by reference. The breathable barrier of Braun et al. is a multilayered, clothlike barrier comprised of at least three layers. The first layer is a porous nonwoven web; the second layer, which is joined to one side of the first layer, comprises a continuous film of PVOH; and the third layer, which is joined to either the second layer or the other side of the first layer not joined with the second layer, comprises another porous nonwoven web. The second layer continuous film of PVOH is not microporous, meaning that it is substantially free of voids which connect the upper and lower surfaces of the film.

In other cases, various films can be constructed with micropores therein to provide breathability. The micropores form what is often referred to as tortuous pathways through the film. Liquid contacting one side of the film does not have a direct passage through the film. Instead, a network of microporous channels in the film prevents water from passing, but allows water vapor to pass.

In some instances, the breathable, liquid-impermeable barriers are made from polymer films that contain any suitable substance, such as calcium carbonate. The films are made breathable by stretching the filled films to create the microporous passageways as the polymer breaks away from the calcium carbonate during stretching. In some embodiments, the breathable film layers can be used in thicknesses of from about 0.01 mils to about 5 mils, and in other embodiments, from about 0.01 mils to about 1.0 mils.

An example of a breathable, yet fluid penetration-resistant material is described in U.S. Pat. No. 5,591,510 to Junker et al., which is incorporated herein by reference. The fabric material described in Junker et al. contains a breathable outer layer of paper stock and a layer of breathable, fluid-resistant nonwoven material. The fabric also includes a thermoplastic film having a plurality of perforations which allow the film to be breathable while resisting direct flow of liquid therethrough.

In addition to the films mentioned above, various other breathable. films can be utilized in the present invention. One type of film that may be used is a nonporous, continuous film, which, because of its molecular structure, is capable of forming a vapor-permeable barrier. Among the various polymeric films which fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. Although the inventors do not intend to be held to a particular mechanism of operation, it is believed that films made from such polymers solubilize water molecules and allow transportation of those molecules from one surface of the film to the other. Accordingly, such films may be sufficiently continuous, i.e., nonporous, to make them liquid-impermeable but still allow for vapor permeability.

Still, other breathable, liquid-impermeable barriers that can be used in the present invention are disclosed in U.S. patent application Ser. No. 08/928,787 entitled "Breathable, Liquid-Impermeable, Apertured Film/Nonwoven Laminate and Process for Making the Same", which is incorporated herein in its entirety by reference. For example, breathable films and/or apertured films can be utilized in the present invention. Such films can be included within a laminate structure. In one embodiment, a breathable, liquid-impermeable, apertured film/nonwoven laminate material can be formed from a nonwoven layer, an apertured film layer, and a breathable film layer. The layers may be arranged so that the apertured film layer or the breathable film layer is attached to the nonwoven layer.

For instance, in one embodiment, an apertured film can be used in the present invention that is made from any thermoplastic film, including polyethylene, polypropylene, copolymers of polypropylene or polyethylene, or calcium carbonate-filled films. The particular aperturing techniques utilized to obtain the apertured film layer may be varied. The film may be formed as an apertured film or may be formed as a continuous, non-apertured film and then subjected to a mechanical aperturing process.

Moisture barrier layers, as described above, can be used alone or incorporated into a laminate when used to construct the dental wipe of the present invention. When incorporated into a laminate, the laminate can include various nonwoven webs in combination with the moisture barrier layer. For instance, moisture barrier laminates can be formed from many processes such as for example, meltblowing processes, spunbonding processes, coforming processes, spunbonding/meltblowing/spunbonding processes (SMS), spunbonding/meltblowing processes (SM), and bonded carded web processes. For instance, in one embodiment, the nonwoven layer of a laminate moisture barrier of the present invention is a spunbond/meltblown/spunbond (SMS) and/or spunbond/meltblown (SM) material. An SMS material is described in U.S. Pat. No. 4,041,203 to Brock et al. which is incorporated herein in its entirety by reference. Other SMS products and processes are described for example in U.S. Pat. No. 5,464,688 to Timmons et al., U.S. Pat. No. 5,169,706 to Collier et al. and U.S. Pat. No. 4,766,029 to Brock et al., all of which are also incorporated herein in their entireties by reference. Generally, an SMS material will contain a meltblown web sandwiched between two exterior spunbond webs. Such SMS laminates are available from Kimberly-Clark Corporation under marks such as Spunguard7 and Evolution7. The spunbonded layers on the SMS laminates provide durability and the internal meltblown barrier layer provides porosity and additional clothlike feel. Similar to an SMS laminate, an SM laminate is essentially a spunbond layer laminated to a meltblown layer.

In forming a dental wipe of the present invention with a moisture barrier, the barrier can be bonded together with the other layers of the wipe in a number of various ways.

Thermal bonding, adhesive bonding, ultrasonic bonding, extrusion coating, and the like, are merely examples of various bonding techniques that may be utilized in the present process to attach the moisture barrier to the fibrous layers of the dental wipe.

In some embodiments, any of the above layers and/or materials can also be dyed or colored so as to form a base web or moisture barrier having a particular color. For example, in one embodiment, the moisture barrier can be provided with a colored background. For instance, white tufts, colored tufts, and/or a white titanium oxide background could be utilized.

As described above, the dental wipe of the present invention can be made from various components and contain various features. For instance, the dental wipe can include a non-elastic component, an elastic component and a moisture barrier. If desired, a texturized surface can be located on the dental wipe for facilitating the scrubbing and cleaning of teeth and gums. Further, the dental wipe can be made from single layer materials or laminates which, in turn, can be made from various materials and fibers. One particular embodiment of a dental wipe made in accordance with the present invention will now be discussed with reference to FIG. 2.

In this embodiment, the dental wipe 10 includes the first section 20 thermally bonded to the second section 30. The second section 30 is designed for contacting the teeth and gums of the user, while the first section 20 is made from an elastic laminate for providing the dental wipe with form fitting properties.

More particularly, the second section 30, in this embodiment, is a three layered laminate. The laminate includes an interior polypropylene spunbond layer, a middle moisture barrier layer, and an outer layer that forms an exterior surface of the dental wipe.

The polypropylene spunbond layer is made from spunbond polypropylene filaments and can have a basis weight of from about 0.3 osy to about 1.0 osy, and can particularly have a basis weight of about 0.5 osy. The moisture layer, on the other hand, can be a film made from linear low-density polyethylene containing a calcium carbonate filler. The film can be stretched in order to create pores for making the film breathable while remaining substantially impermeable to liquids. The moisture barrier layer can have a basis weight of from about 0.2 osy to about 1.0 osy, and particularly can have a basis weight of about 0.5 osy. The polypropylene spunbond layer can be adhesively secured to the moisture barrier layer.

In an alternative embodiment, the interior polypropylene spunbond layer can be replaced with a nonwoven web made from polypropylene/polyethylene bicomponent fibers. The middle moisture barrier layer, on the other hand, can be a film made from a mixture of polymers, such as CATALLOY film marketed by the Pliant Corporation.

The exterior layer can be a spunbond or through air bonded web made from bicomponent polyethylene/polypropylene filaments in a side-by-side arrangement. The exterior layer can have a basis weight of from about 1.0 osy to about 5.0 osy, and can particularly have a basis weight of from about 2.0 osy to about 4.0 osy. Alternatively, the exterior layer itself can be a laminate structure. For example, a two-banked process can be used in which a layer of larger diameter fibers is formed on a layer of small diameter fibers.

The exterior bicomponent spunbond layer can be laminated to the other layers using a thermal or ultrasonic point bonding process, such as a point unbonded pattern process. More particularly, the layers can be point unbonded to form a texturized surface. For instance, as shown in FIG. 2, the point unbonded pattern can be designed to form circular tufts which protrude from the surface of the laminate.

As mentioned above, the first section 20 is an elastic laminate. For instance, the first section 20 can be a stretch bonded laminate sheet. The stretch bonded laminate sheet can include elastic threads made from an elastomeric material sandwiched between two polypropylene spunbond layers. The elastic threads can be, for instance, made from a styrene-ethylene butylene-styrene block copolymer, such as KRATON G2740 available from the Shell Chemical Company. The stretch bonded laminate can have a basis weight of from about 1.0 osy to about 5 osy, particularly from about 1.5 osy to about 3.5 osy, and more particularly from about 2.0 osy to about 3.0 osy.

Instead of a stretch bonded laminate sheet, the first section 20 can also be a neck bonded laminate sheet. The neck bonded laminate sheet can include a metallocene catalyzed elastic polyethylene film sandwiched between two polypropylene spunbond layers. The spunbond layers can have a basis weight of about 0.45 osy prior to being stretched. The polyethylene film, on the other hand, can have a basis weight from about 0.5 osy to about 1.5 osy.

The first section 20 can be attached to the second section 30 using various methods. For example, as shown in FIG. 2, the first section 20 can be ultrasonically bonded to the second section 30 along the outer edges in order to form a pocket for the insertion of a finger.

Once the first section 20 and the second section 30 are bonded together, excess material can be cut and removed from the dental wipe. In general, any suitable cutting method can be used in order to trim away excess material. For example, the material can be cut using a high pressure jet of water referred to as a water knife or can be cut using a conventional mechanical device, such as a cutter or a pair of shears. In one embodiment, the first section 20 and the second section 30 can be simultaneously bonded together and cut from the materials from which they are made. For instance, ultrasonic energy can be used to bond and cut materials in one step.

The dimensions of the dental wipe that is formed in accordance with the present invention will depend upon the particular application and purpose for which the dental wipe is to be used. For instance, the dental wipe can be constructed in order to fit around the finger of an adult or the finger of a child. Further, the dental wipe can also be constructed to fit around two fingers. For most single finger dental wipes, the wipe should have a length of from about 1 inch to about 5 inches and a median flattened width of from about 0.5 inches to about 1.5 inches. When constructed to fit around two fingers, the dental wipe can have a median width of from about 0.75 inches to about 2.5 inches, depending on the elasticity of the wipe.

Figure 11:
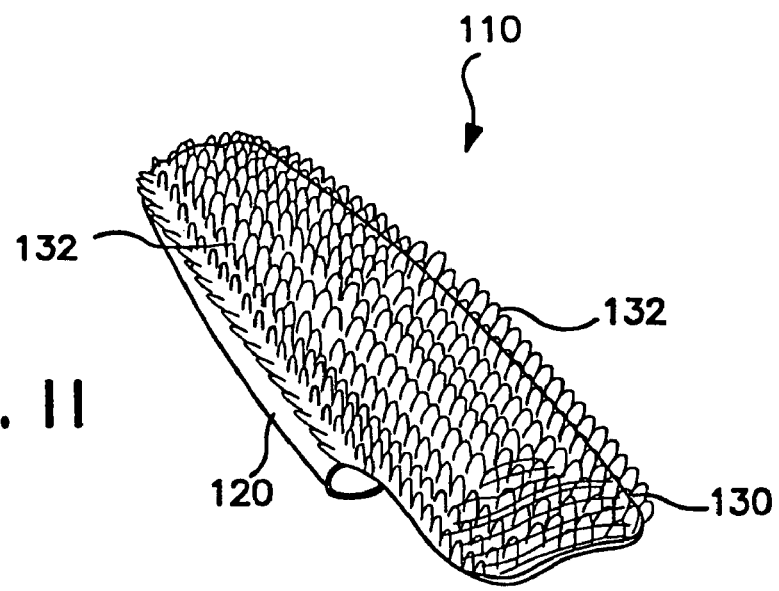
FIG. 11 is a perspective view of a further alternative embodiment of a dental wipe made in accordance with the present invention.
Figure 12:
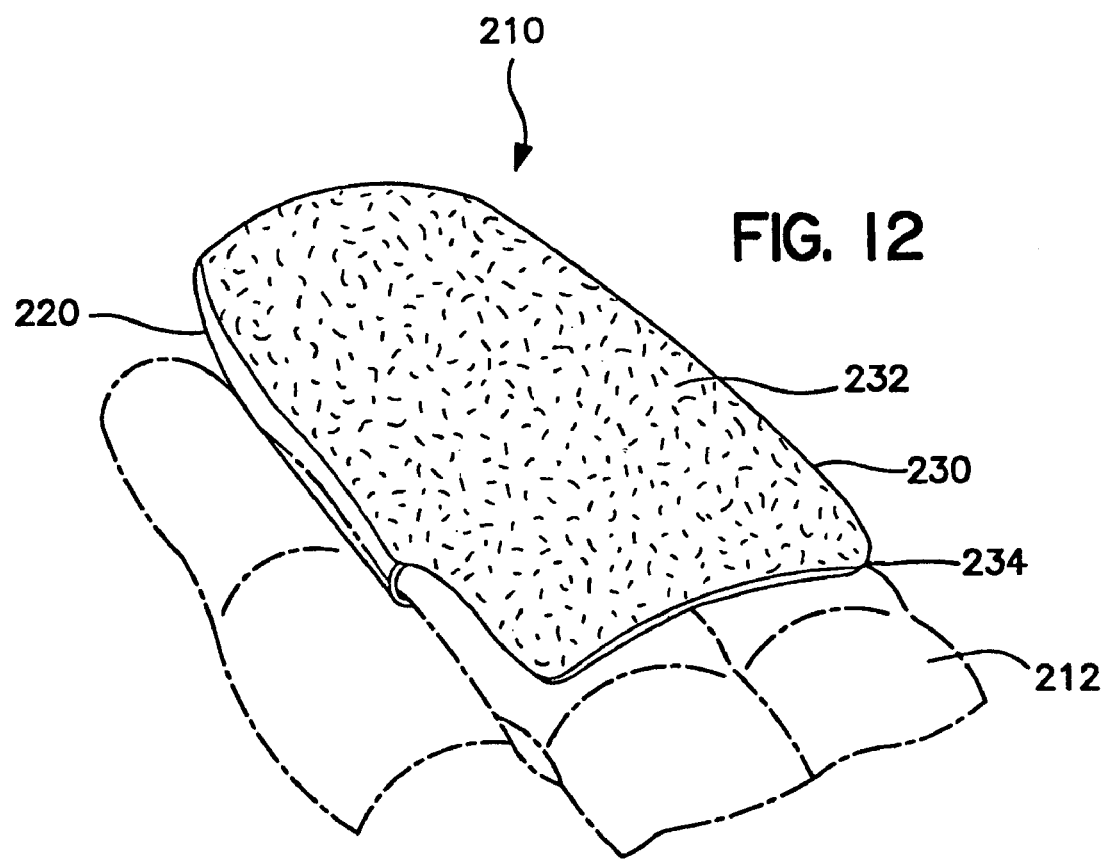
FIG. 12 is a perspective view of another alternative embodiment of a dental wipe made in accordance with the present invention which is adapted to be placed over two fingers.
Figure 13:
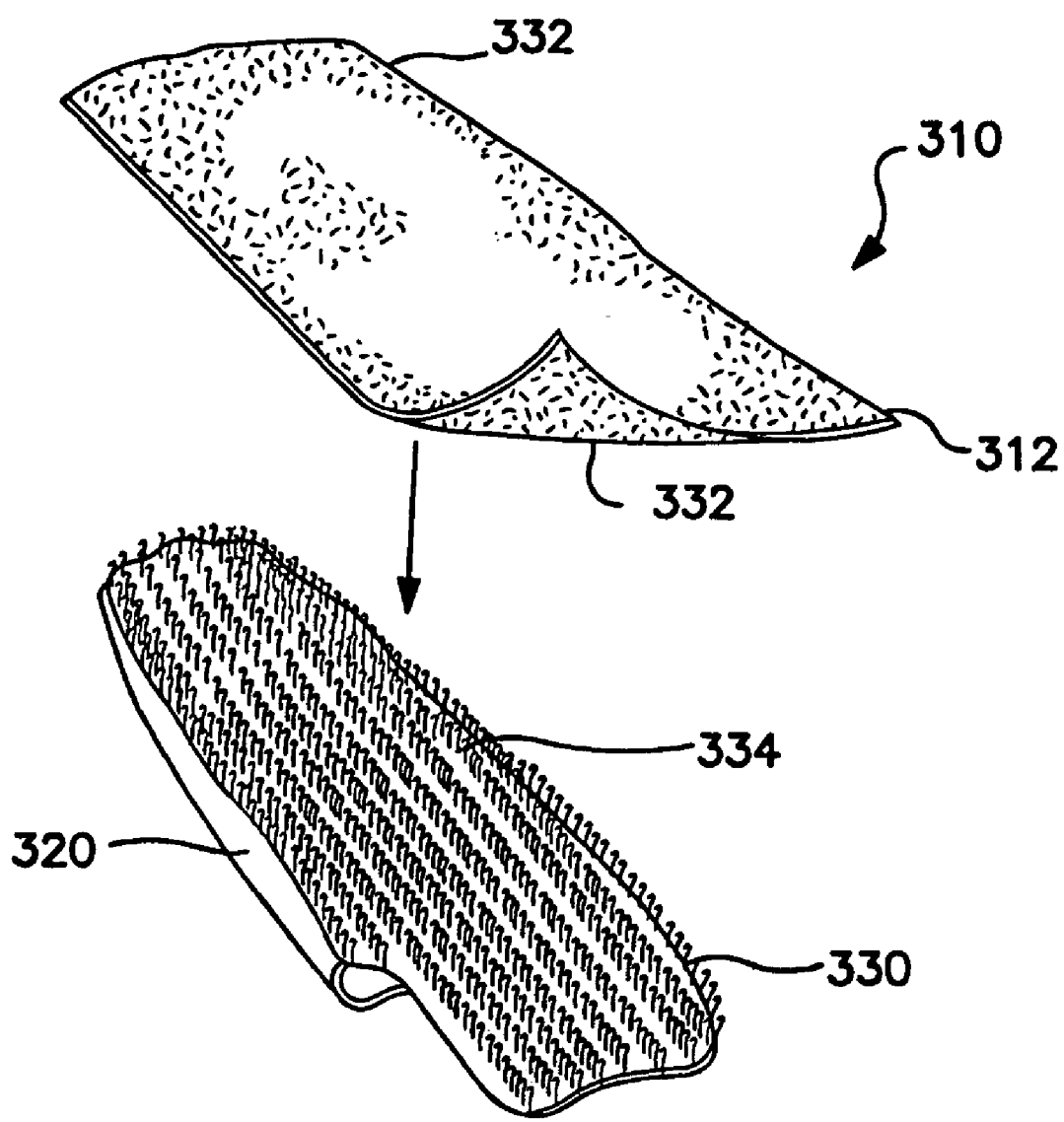
FIG. 13 is a perspective view of another alternative embodiment of a dental wipe made in accordance with the present invention.

Referring now to FIGS. 11–13, three further embodiments of dental wipes made in accordance with the present invention are shown. In these embodiments, the texturized material is a looped material. For instance, referring to FIG. 11, a dental wipe generally 110 is shown. The dental wipe 110 includes a first section 120 thermally bonded, stitched or otherwise connected to a second section 130. The second section 130 includes a texturized surface which is a looped material containing a plurality of bristles 132.

In this embodiment, the looped material 130 represents a knitted fabric. The looped bristles 132 are arranged in a systematic pattern on the material. In particular, the looped bristles 132 form rows along the surface of the dental wipe 110.

As shown in FIG. 11, the bristles 132 are located over the entire surface of the second section 130. It should be understood, however, that the looped bristles can be placed in a particular area, such as only at the tip of the dental wipe or over all surfaces of the dental wipe. For example, the area occupied by the looped bristles can have a circular, oval or any other suitable shape.

The first section 120 can be made from various materials. For example, in one embodiment, the first section 120 can be made from an elastic material, such as a stretch bonded laminate.

Referring to FIG. 12, another alternative embodiment of a dental wipe generally 210 is shown. In this embodiment, the dental wipe 210 is configured to fit around a pair of fingers 212.

The dental wipe 210 includes a first section 220 and a second section 230. The second section 230 is a looped material containing looped bristles 232. In this embodiment, the looped bristles 232 are densely packed on the looped material 230 and are randomly arranged. The looped material 230 is similar to a loop material used in a hook and loop fastener. As shown, the loop material 230 not only includes looped bristles 232 but also a base layer 234. The base layer 234 can be made from various fabrics, including, elastic fabrics, such as spandex fabrics.

Referring to FIG. 13, a further alternative embodiment of a dental wipe generally 310 is shown. In this embodiment, the dental wipe 310 includes a first section 320 connected to a second section 330. The second section 330 includes a plurality of hooks 334. In one embodiment, the surface containing the hooks could be used for cleaning one's teeth.

In an alternative embodiment, the dental wipe 310 further includes a looped material 312 containing looped bristles 332. As shown, the looped bristles 332 are disposed about both sides of the looped material 312. In this manner, one side of the looped material 312 can be attached to the second section 330 through a hook and loop fastening mechanism. Once applied to the second section 330, the looped material can then be used as a cleaning surface.

In this embodiment, the loop material 312 can be removed from the dental wipe 310 and replaced as desired. Consequently, this embodiment generally refers to a dental wipe having a reusable component.

In an alternative embodiment to the dental wipe illustrated in FIG. 13, the second section 330, instead of including a plurality of hooks 334, can be made from a nonwoven material defining a loop fastening-like surface. In this embodiment, the material 312 can include looped bristles 332 on one side of the material and can include hook fasteners on the opposite side of the material. In this manner, the hooks located on the material 312 can be secured to the surface of the second section 330.

In the embodiments illustrated in FIGS. 11, 12 and 13, the material containing the loop bristles can either be non-elastic or elastic. When using an elastic material containing loop bristles, however, the entire dental wipe can be made from the material. For example, the elastic material containing the loop bristles, such as VELSTRETCH Tape, 9999 or MEDFLEX Tape, 9399 available from VELCRO, USA, Inc., can be formed into a tubular shape and then bonded along the edges. The resulting product will have form-fitting properties and will have an exterior, scrubbing surface comprised of the looped bristles.

In still a further embodiment, hook structures can be laminated to the backing of an elastic material containing loop bristles as described above. In this embodiment, the elastic looped material can be wrapped around a finger and secured to itself using the hook structures. Once secured to a finger, the material can be used to scrub an adjacent surface.

Figure 16:
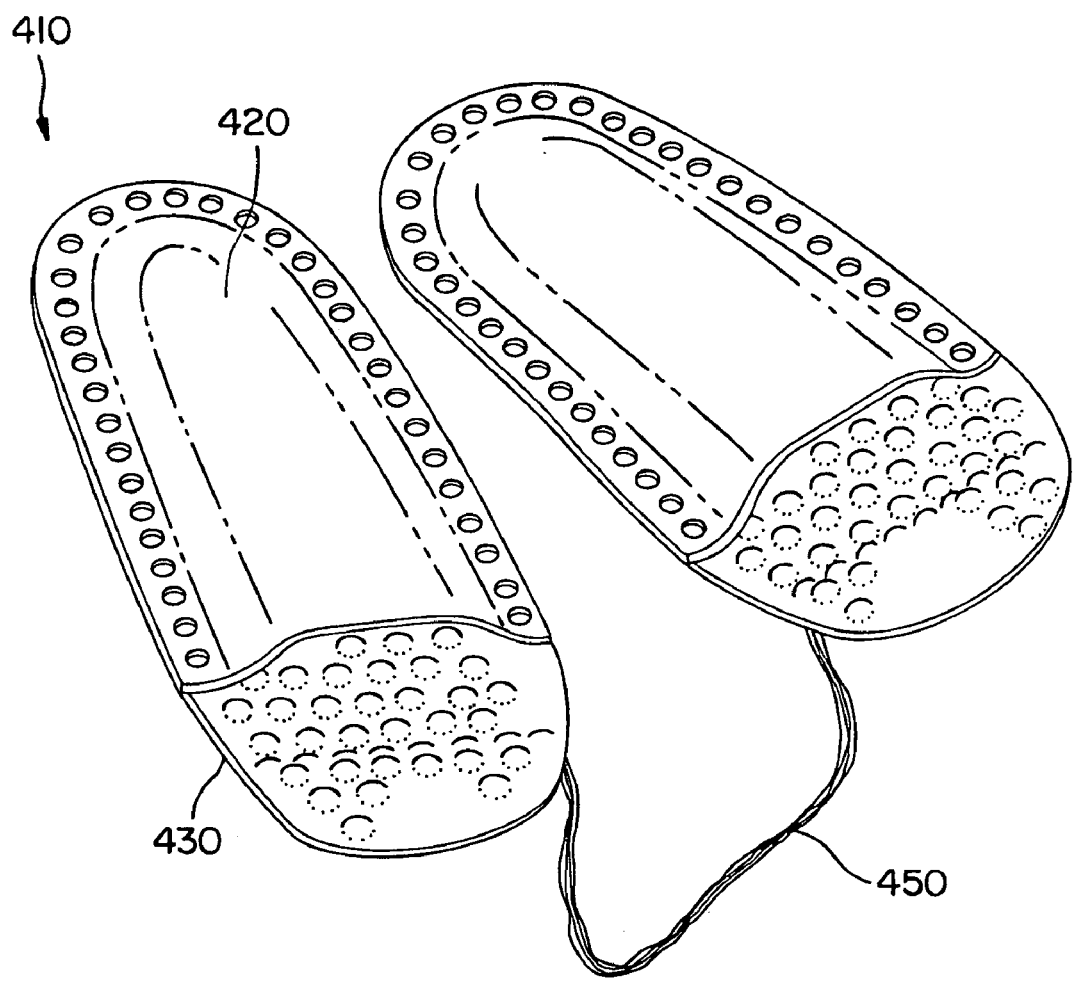
FIG. 16 is a perspective view of another alternative embodiment of a dental wipe made in accordance with the present invention.

A still further embodiment of a dental wipe generally 410 made in accordance with the present invention is illustrated in FIG. 16. As shown, dental wipe 410 is a two-fingered wipe. Specifically, the dental wipe 410 includes two monofingered wipes attached together so that both sides of the teeth can be cleaned at the same time. Each of the wipes includes a first section 420 bonded to a second section 430 defining a textured surface. The two wipes are connected together by a connecting portion 450. In one embodiment, the connecting portion 450 can be made from dental floss.

In order to provide better dental care to the teeth being cleaned, a variety of chemical additives can be applied to the dental wipe of the present invention. For example, in one embodiment, cationic polymers can be coated onto the dental wipe. Cationic polymers can help clean teeth and/or gums because they typically have a strong attraction for negatively charged bacteria and deleterious acidic by-products that accumulate in plaque. One example of a cationic polymer that is suitable for use in the present invention is chitosan (poly-N-acetylglucosamine, a derivative of chitin) or chitosan salts. Chitosan and its salts are natural biopolymers that can have both hemostatic and bacteriostatic properties. As a result, chitosan can help reduce bleeding, reduce plaque, and reduce gingivitis.

In addition to chitosan and chitosan salts, any other cationic polymer known in the art can generally be applied to a dental wipe of the present invention. For example, in one embodiment, cationic starches are used in the present invention. One such suitable cationic starch is, for example, COBOND, which can be obtained from National Starch. In another embodiment, cationic materials that are oligomeric compounds can be used. In some embodiments, combinations of cationic materials can be utilized.

In addition to the chemical additives mentioned above, a variety of other additives can be applied to a dental wipe of the present invention. For instance, other well known dental agents can be utilized. Examples of such dental agents include, but are not limited to alginates, soluble calcium salts, phosphates, fluorides, such as sodium fluoride (NaF) or stannous fluoride (SnF2), and the like. Moreover, mint oils and mint oil mixtures can be applied to the dental wipe of the present invention. For instance, in one embodiment, peppermint oil can be applied to the dental wipe. Moreover, in another embodiment, a mint oil/ethanol mixture can be applied. Components of mint oil (e.g., menthol, carvone) can also be used. Additionally, various whitening agents can be applied to the dental wipe. Examples of whitening agents include silica, peroxides and in situ sources of peroxide, such as carbamide peroxide.

Furthermore, in some embodiments, the dental wipe can also comprise an anti-ulcer component. In particular, one embodiment of the present invention can comprise a component designed to act as an anti-*H. pylori* agent. In general, any additive known in the art to be an anti-ulcer or anti-*H. pylori* agent can be used in the present invention. In one embodiment, for example, bismuth salts can be utilized. One particularly effective bismuth salt, bismuth subcitrate, is described in more detail in U.S. Pat. No. 5,834,002 to Athanikar, which is incorporated herein in its entirety by reference thereto. Another example of a suitable bismuth salt is PEPTO-BISMOL sold by The Procter & Gamble Company, containing bismuth subsalicylate. In addition to bismuth salts, other examples of suitable anti-ulcer additives include, but are not limited to, tetracycline, erythromycin, clarithromycin, omeprazole, metronidazole, or other antibiotics. Furthermore, any additive useful for treating peptic ulcers, such as H2-blockers, sucralfate, and the like, can be used as well.

Besides the above additives, other additives can also be applied to the dental wipe. Such materials can include, but are not limited to, flavoring agents, preservatives, anti-microbial agents, polishing agents, hemostatic agents, anti-plaque agents, anti-caries agents, antibiotics, antioxidants, desensitizers, lubricants, remineralization agents, tartar control agents, surfactants, etc. Examples of suitable flavoring agents include various sugars, breath freshening agents, menthol, carvone, anise oil, anethole, methyl salicylate, thymol and artificial sweeteners as well as natural flavorants, such as cinnamon, vanilla and citrus. Moreover, in one embodiment, xylitol, which provides a cooling effect upon dissolution in the mouth and is anti-cariogenic, can be used as the flavoring agent. As stated, preservatives, such as methyl benzoate or methyl paraben, can also be applied to a dental wipe of the present invention.

Suggested polishing agents include but are not limited to, silica and sodium bicarbonate. Suggested anti-microbial agents or anti-bacterial agents include, but are not limited to, triclosan, thymol, eucalyptol, menthol, methyl salicylate, chlorhexidine, hexetidine, hydrogen peroxide and carbamide peroxide. Suggested anti-caries agents include, but are not limited to, triclosan, xylitol, and fluoride. Suggested anti-plaque agents include, but are not limited to, triclosan, menthol, thymol, eucalyptol, methyl salicylate and cetylpyridinium chloride.

In addition, a variety of other additives and combinations thereof can be applied to a dental wipe of the present invention. For instance, examples of various materials that can be utilized as additives in the present invention are described in U.S. Pat. No. 3,902,509 to Tundermann et al. and U.S. Pat. No. 5,445,825 to Copelan et al., which are incorporated herein by reference. Although various specific additives have been specifically mentioned above, it should be understood that any additive can generally be applied to the dental wipe of the present invention. The additives can be applied to the dental wipe as is or they can be encapsulated in order to preserve the additives and/or to provide the additive with time release properties.

In general, the chemical additives described above can be applied to a dental wipe of the present invention according to a number of ways known in the art. For example, the additives can be applied to the wipe using a saturant system, such as disclosed in U.S. Pat. No. 5,486,381 to Cleveland et al., which is incorporated herein by reference. Moreover, the additives can also be applied by various other methods, such as print, blade, roll, spray, spray-drying, foam, clean treating applications, etc., which are well known in the art. The additives can further be applied as a mixture of molten solids or co-extruded onto the wipe. Additionally, in another embodiment, the chemical additives can be impregnated into the material during manufacturing as is well known in the art. It should be understood that when coated onto a wipe as s described above, the additives can be applied to the base web before or after the base web is stamped or bonded to form the dental wipe of the present invention. Furthermore, it should also be understood that, if desired, various additives, solutions, and chemicals can be applied by the consumer to the wipe just before use.

In another embodiment, the additive is encapsulated and then applied to the dental wipe. Encapsulation is a process by which a material or mixture of materials is coated with or entrapped within another material or mixture of materials. The technique is commonly used in the food and pharmaceutical industries. The material that is coated or entrapped is normally a liquid, although it can also be a solid or gas, and is referred to herein as the core material. The material that forms the coating is referred to as the carrier material. A variety of encapsulation techniques are well-known in the art and can be used in the current invention, including spray drying, spray chilling and cooling, coacervation, fluidized bed coating, liposome entrapment, rotational suspension separation, and extrusion.

Spray drying is commonly used for encapsulating food and flavors. To prepare a material for spray drying, the carrier material is dissolved in an aqueous solution. The core ingredient is added to this solution and mixed thoroughly. A typical load of carrier to core material is 4:1, although much higher or lower loads can be used. The mixture is homogenized, and then fed into a spray dryer where it is atomized and released into a stream of hot air. The water is evaporated, leaving a dried particle comprising the core material trapped within the carrier matrix.

Suitable carrier materials include but are not limited to gums, gum Arabic, modified starches, gelatin, cellulose derivatives, and maltodextrins. Suitable core materials include but are not limited to flavors, natural oils, additives, sweeteners, stabilizers besides the other various additives mentioned above.

Regardless of the mechanism utilized to apply the chemical additives to the wipe, the additives can be applied to the wipe via an aqueous solution, non-aqueous solution, oil, lotion, cream, suspension, gel, etc. When utilized, an aqueous solution can contain any of a variety of liquids, such as various solvents and/or water. Moreover, the solution can often contain more than one additive. In some embodiments, the additives applied by an aqueous solution or otherwise constitute approximately less than 80% by weight of the dental wipe. In other embodiments, the additives can be applied in an amount less than about 50% of the weight of the wipe.

Moreover, in some embodiments, the additives can also be applied asymmetrically onto the wipe to reduce costs and maximize performance of the wipe. For instance, in one embodiment, a flat sheet of the base web is asymmetrically contacted with a particular coating agent, and thereafter stamped and bonded to form the dental wipe of the present invention, wherein only the surface used to clean teeth is coated with the additives. In another embodiment, the finger wipe is stamped and bonded, and thereafter asymmetrically coated with a particular coating agent.

Prior to being shipped and sold, the dental wipe of the present invention can be placed in various sealed packaging in order to preserve any additives applied to the dental wipe or otherwise to maintain the dental wipe in a sterile environment. Various packaging materials that can be used include ethylene vinyl alcohol (EVOH) films, film foil laminates, metalized films, multi-layered plastic films, and the like. The packaging can be completely impermeable or can be differentially permeable to the flavorants depending on the application.

The present invention may be better understood by reference to the following examples:

EXAMPLES

Various dental wipes were made according to the present invention and tested. The dental wipes were made with various materials as described in the following examples. The dental wipes were made from the materials using ultrasonic welding to form the seams. In each of the following examples, unless otherwise specified, each dental wipe was made from a mold having a length of from about 2.75 inches to about 3.0 inches. The dental wipes were made with an open end for the insertion of the finger and a closed end. The width or circumference of the dental wipe tapered inwardly from the open end to the closed end. The width of the mold at the opening ranged from about 1.063 inches to about 1.25 inches. The width at the closed end ranged from about 0.8 inches to about 0.9 inches. After being formed, the dental wipes were cut to a length of from about 1.0 inches to about 3.0 inches. The width at the opening normally ranged from about 0.6 inches to about 1.0 inches (internal diameter). When containing a pull-on tab, the length of the tab ranged from about 0.2 to about 0.8 inches.

Example 1

A dental wipe of the present invention was formed as follows. Specifically, a first section made from a point of unbonded spunbond laminate materials was ultrasonically welded to a stretch-bonded laminate (SBL) sheet using a Branson 920 IW ultrasonic welder. The point unbonded spunbond laminate formed the front of the dental wipe, while the SBL sheet formed the back of the dental wipe. An example of a point unbonded laminate is described in U.S. Pat. No. 5,858,515, which is incorporated herein by reference.

The point unbonded spunbond laminate was formed by thermally bonding together a polypropylene spunbond web, a breathable film sheet, and a bicomponent spunbond web. The breathable film sheet was placed in between the spunbond webs.

The polypropylene spunbond web had a basis weight of 0.5 osy the bicomponent spunbond web was made from a polyethylene component and a polypropylene component in a side-by-side relationship. The bicomponent spunbond web had a basis weight of 2.5 osy. The breathable film sheet was made from a linear low density polyethylene containing a calcium carbonate filler. The film was stretched to form a microporous film. The film had a basis weight of 0.5 osy.

The bicomponent spunbond web was thermally bonded to the film laminate using a point-unbonded pattern that created texture. In particular, generally circular tufts were formed on the laminate. During bonding, a top bond roll having the point-unbonded pattern was heated to 260° F. while the bottom bond roll was heated to 240° F.

The SBL sheet, on the other hand, included threads of an elastic material sandwiched between two polypropylene spunbond layers. The elastic material used was KRATON G2740 S-EB-S glycopolymer available from the Shell Oil Company. The SBL sheet had a basis weight of 2.5 osy. An imprinted, magnesium bond plate served as an anvil for ultrasonic bonding of the SBL sheet to the point unbonded spunbond laminate.

The bicomponent spunbond layer of the point unbonded spunbond material was placed adjacent to the SBL sheet during the ultrasonic welding process, which placed the texturized nubs against the SBL sheet. After ultrasonic welding, excess material was trimmed around the edges and the dental wipe was inverted to place the seam on the inside and the texturized nubs on the outside. Peppermint oil was applied to the dental wipe, which was subsequently used to clean the mouth of an adult.

Example 2

A dental wipe as described in Example 1 was constructed and treated with peppermint oil. The dental wipe was then subsequently used by an adult to clean the mouth of a toddler.

Example 3

A dental wipe made according to Example 1 was constructed. The dental wipe was dipped into drippings from sliced steak and then used by an adult to clean the mouth of a dog.

Example 4

A dental wipe as described in Example 1 was constructed. In this example, however, the bicomponent spunbond sheet of the point unbonded spunbond laminate had a basis weight of 3.6 osy. During the point unbonded process, the top bond roll was heated to 270° F., while the bottom bond roll was heated to 240° F. After being formed, the dental wipe was inverted and treated with peppermint oil. The dental wipe was then subsequently used to clean the mouth of an adult.

Example 5

A dental wipe was constructed similar to the dental wipe described in Example 1. In this embodiment, however, the bicomponent spunbond sheet of the point unbonded spunbond laminate was a through air bonded bicomponent fibrous web having a basis weight of 1.8 osy. The bicomponent filaments contained a polyethylene component and a polypropylene component in a side-by-side relationship. During the point unbonded process, the top bond roll was heated to 260° F. while the bottom bond role was heated to 240° F. After the dental wipe was formed, the glove was inverted so that the texturized nubs as described in Example 1 were placed on the outside.

Example 6

A dental wipe as described in Example 5 was constructed. In this example, however, the through air bonded bicomponent fibrous web had a basis weight of 2.5 osy. Further, the bicomponent web was yellow-pigmented.

Example 7

A dental wipe as described in Example 1 was constructed. In this example, however, the point unbonded spunbond laminate was replaced with a multi-layered material that included a spunbond-meltblown-spunbond laminate that was adhesively laminated to a strip of loop material from a hook and loop fastener. The spunbond-meltblown-spunbond laminate had a total basis weight of 1.0 osy. The laminate included a 0.4 osy meltblown interior layer made from polypropylene fibers. The two spunbond facings were also made from polypropylene.

The loop material was VELCRO loop 2000 material obtained from VELCRO USA, Inc.

The resulting multi-layered material was ultrasonically welded to the stretch-bonded laminate described in Example 1, such that the spunbond-meltblown-spunbond layer was positioned adjacent to the stretch-bonded layer. The loop material formed a facing of the dental wipe. The dental wipe was then treated with a flavor formulation containing spearmint and peppermint oils and then was subsequently used to clean the mouth of an adult.

Example 8

A dental wipe as described in Example 1 was constructed. In this example, however, the point unbonded spunbond laminate was replaced with a coform sheet. The coform sheet was a meltblown web containing 50% pulp fibers and 50% by weight polypropylene fibers. The coform sheet had a basis weight of 1.2 osy. The coform sheet was ultrasonically Welded to the stretch-bonded laminate described in Example 1.

In this example, the dental wipe was not inverted. Further, the section of the dental wipe made from the coform sheet was longer than the section made from the stretch-bonded laminate creating a pull-on tab. The dental wipe was then subsequently used to apply a petroleum lotion to an infant after a diaper change.

Example 9

A dental wipe was constructed similar to the dental wipe described in Example 1. In this example, the bicomponent spunbond web contained in the point unbonded spunbond laminate had a basis weight of 3.5 osy. During the point unbonded process, the top bond roll was heated to 270° F., while the bottom bond roll was heated to 250° F.

In contrast to Example 1, however, instead of using a stretch-bonded laminate sheet, the point unbonded spunbond laminate was ultrasonically welded to a neck-bonded laminate. The neck-bonded laminate was formed by adhesively bonding a 15 gsm polyurethane film between a pair of opposing polypropylene spunbond facings. The adhesive used to form the neck-bonded laminate was Findley H2525A adhesive obtained from Findley, Inc. The spunbond facings had a basis weight of 0.5 osy prior to being stretched or necked. The spunbond facings were necked to a width corresponding to 30% of their original width.

After the point unbonded spunbond laminate was welded to the neck-bonded laminate, the dental wipe was inverted so that the texturized nubs formed an exterior face of the dental wipe. Peppermint oil was then applied to the dental wipe which was subsequently used to clean the mouth of an adult.

Example 10

A dental wipe was constructed similar to the dental wipe described in Example 1, using the same point unbonded spunbond laminate. In contrast to Example 1, however, instead of using a stretch-bonded laminate as the elastic material, a neck-bonded laminate was used. The point unbonded spunbond laminate was ultrasonically welded to the neck-bonded laminate.

The neck-bonded laminate contained a 35 gsm metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 45% of the original width.

After the point unbonded spunbond laminate was welded to the neck-bonded laminate, the dental wipe was inverted so that the texturized nubs formed an exterior face of the dental wipe. Peppermint oil was then applied to the dental wipe which was subsequently used to clean the mouth of an adult.

Example 11

A dental wipe similar to the dental wipe described in Example 9 was constructed. In this example, however, the neck-bonded laminate sheet was formed by adhesively bonding a 15 gsm polyether amide elastic film (PEBAX-2533 film obtained from Elf Atochem) to a pair of opposing bidirectionally extensible polypropylene spunbond facings. The polypropylene spunbond facings had a basis weight of 0.3 osy prior to being stretched or necked. When attached to the elastic film, the spunbond facings were necked to a width corresponding to 40% of their original width and then crimped an amount to produce a 50% reduction in length.

The neck-bonded laminate was ultrasonically welded to the point unbonded spunbond laminate. The resulting dental wipe was inverted and treated with peppermint oil. It was observed that the neck-bonded laminate sheet had a elastic properties in two dimensions. The dental wipe was subsequently used to clean the mouth of an adult.

Example 12

A dental wipe as described in example 1 was constructed from a point unbonded spunbond laminate ultrasonically welded to a stretch-bonded laminate. The total basis weight for the point unbonded spunbond sheet was 2.75 osy.

The dental wipe was applied with the following additives:

| Additive | Wt % |
| --- | --- |
| Peppermint oil (obtained from Global Essence, Inc.) | 0.51 |
| 1% Chitosan citrate solution (formed from chitosan made by Vanson Chemical Company and citric acid made by Archer Daniels Midland) | 0.07 |
| T MAZ-80 Polysorbate Surfactant (obtained from BASF) | 0.55 |
| Xylitol (obtained from Cultor, Inc.) | 8.56 |
| Water | 90.31 |

After being immersed in the above aqueous solution, the finger wipe was allowed to dry and sealed in a plastic film. After a period of time, the finger wipe was removed and used in the mouth of a subject.

Example 13

In this example, a dental wipe of the present invention was formed from a single sheet of material. In particular a stretch-bonded laminate as described in Example 1 was folded upon itself and ultrasonically welded in a J-shape. The resulting dental wipe was closed at one end and open at the other end in order to form a pocket for the insertion of a finger. One side of the open end of the dental wipe was kept longer than the other side to facilitate pulling the glove on to a finger. The dental wipe had a tapered width. Specifically, the dental wipe had a length of about 5.7 centimeters and a width at the opening for the insertion of a finger of about 2.4 centimeters (internal width).

Example 14

A dental wipe similar to the one described in Example 1 was constructed. In this example, the point unbonded spunbond laminate had a total basis weight of 2.75 osy. Further, instead of being welded to a stretch-bonded laminate, the point unbonded spunbond laminate was adhesively secured to a elastomeric, melt blown polyether ester film (ARNITEL EM400 polyether ester obtained from DSM Engineering Plastics). The melt blown polyether ester web had a basis weight of about 2 osy.

Example 15

A dental wipe similar to the one described in Example 1 was constructed. In this embodiment, the point unbonded spunbond laminate had a total basis weight of 2.75 osy.

In this example, the point unbonded spunbond laminate was welded to a spunbond-meltblown-spunbond laminate that had been adhesively bonded to a thin strip of an elastic material commonly used as leg elastics in diapers. Specifically, the spunbond-meltblown-spunbond laminate had a total basis weight of 1.0 osy wherein the meltblown interior layer had a basis weight of 0.4 osy. The elastic strip was 1 centimeter in width and was adhesively bonded to the spunbond-meltblown-spunbond laminate. The elastic strip included elastic threads sandwiched between two polypropylene spunbond facings.

The resulting dental wipe made by welding the spunbond-meltblown-spunbond laminate to the point unbonded spunbond sheet was elastic because of the elastic strip attached to the spunbond-meltblown-spunbond laminate. The elastic strip was not uniformly elastic. The dental wipe was made so that the elastic strip rested between the first and second knuckles of the finger of an adult after insertion of the finger into the dental wipe.

Example 16

An alternative embodiment of a dental wipe made in accordance with the present invention was formed as follows. In this example, the dental wipe included a first section made from a spunbond-meltblown-spunbond laminate welded to a second section made from a neck-bonded laminate. The spunbond-meltblown-spunbond laminate formed the front side of the dental wipe, while the neck-bonded laminate formed the back side.

The spunbond-meltblown-spunbond laminate was made from polypropylene and had a total basis weight of 0.8 osy.

The neck-bonded laminate on the other hand, was similar to the neck-bonded laminate described in Example 10, except that it had a heavier weight film and heavier weight facings to have an overall basis weight of 4.2 osy. Further, the facings were necked to a width 40% of their original width.

The two sections were thermally bonded together in the shape of a finger and excess material was trimmed from the edges of the wipe. The wipe was thereafter inverted to place the seams on the inside. The spunbond-meltblown-spunbond laminate section of the dental wipe was longer than the neck-bonded laminate section, such that a pull-on-tab was provided for ease in placing the wipe on a finger. Specifically, the length of the spunbond-meltblown-spunbond laminate section was approximately 5 centimeters while the length of the neck-bonded laminate was approximately 4 centimeters. Upon flattening of the dental wipe, the width at the bottom of the wipe was approximately 2.4 centimeters.

Example 17

A finger glove was constructed similar to the finger glove in Example 1, insofar as an elastic material was welded to a texturized is surface with a finger-shaped design. In contrast to Example 1, however, instead of using a stretch bonded laminate as the elastic material, a neck-bonded laminate was used. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

In further contrast to Example 1, the texturized material was not a point unbonded nonwoven, but rather a knitted nylon material having looped bristles approximately 3 to 4 mm in length. This knitted material had a basis weight of approximately 2.5 osy. The bristles had a consistent directional component, allowing scrubbing in a direction with relatively high or low coefficient of friction, i.e., both with and against "the grain". The looped bristles were fairly homogeneous in size and distribution, and generally extended between 3 mm and 4 mm from the surface. The bristle loops were comprised of multiple filaments.

The knitted material was ultrasonically welded to the neck-bonded laminate. Peppermint oil was then applied to the finger glove, which was subsequently used to clean the mouth of an adult.

Example 18

A finger glove was constructed similar to the finger glove in Example 1, insofar as an elastic material was welded to a texturized surface with a finger-shaped design. In contrast to Example 1, however, instead of using a stretched bonded laminate as the elastic material, a necked bonded laminate was used. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

In further contrast to Example 1, the texturized material was not a point unbonded nonwoven, but rather a knitted nylon material having looped bristles approximately 3 mm in length. This knitted material had a basis weight of approximately 2.5 osy, and was ultrasonically welded around the perimeter to a breathable film laminate (1.0 osy), thereby providing a nonwoven/knit laminate containing looped bristles and a moisture barrier.

The bristled, nonwoven/knit laminate was ultrasonically welded to the neck-bonded laminate such that the looped bristles were adjacent to the NBL. The finger glove was inverted, placing the seam on the inside and the bristles on the outside. A commercially available baby toothpaste (GERBER Tooth & Gum Cleanser) was then applied to the finger glove, which was subsequently used to clean the mouth of a toddler.

Example 19

A finger glove was constructed similar to the finger glove in Example 1. The point unbonded spunbond laminate was ultrasonically welded to a neck-bonded laminate. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

In further contrast to Example 1, the texturized material was a conventional loop fastener, VELCRO Med-Flex Tape 9399, comprised of nylon and Spandex. This material was elastic. The looped bristles were monofilament, and generally extended from 0.5 mm to 3 mm from the surface when unstretched, with some extending to 10 mm when tension was applied.

The knitted material was ultrasonically welded to the neck-bonded laminate. Peppermint oil was then applied to the finger glove which was subsequently used to clean the mouth of an adult.

Example 20

A finger glove was constructed similar to the finger glove in Example 1. In contrast to Example 1, however, instead of using a stretch bonded laminate as the elastic material, a neck-bonded laminate was used. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

In further contrast to Example 1, the texturized material was a laminate comprised of a commercially available loop fastener, VELCRO Loop 002 Tape 0599, approximately 2.5 osy, comprised of nylon adhesively laminated to a breathable film laminate (1.0 osy ).

The texturized material, was ultrasonically welded to the necked bonded laminate. A commercially available baby toothpaste (GERBER) was then applied to the finger glove, which was subsequently used to clean the mouth of a toddler.

Example 21

A finger glove was constructed similar to the finger glove in Example 1. In contrast to Example 1, however, instead of using a stretch bonded laminate as the elastic material, a neck-bonded laminate was used. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width. In further contrast to Example 1, the texturized material was a needle punched nonwoven substrate, with a basis weight of approximately 5 osy.

The texturized material was ultrasonically welded to the necked-bonded laminate. Peppermint oil was then applied to the finger glove, which was subsequently used to clean the mouth of an adult.

Example 22

The ability of a fastening mechanism of the present invention to be attached to a finger toothbrush was demonstrated. A finger toothbrush of the present invention was formed as follows. Specifically, a first section made from a point unbonded polypropylene spunbond material was ultrasonically welded to a stretch-bonded laminate (SBL) sheet using a Branson 920 IW ultrasonic welder. The point unbonded spunbond material formed the front of the toothbrush, while the SBL sheet formed the back of the toothbrush.

The point unbonded spunbond had a total basis weight of about 2.7 osy. The spunbond material was thermally bonded using a point-unbonded pattern that created texture. In particular, circular tufts were formed on the spunbond material. During bonding, a top bond roll having the point-unbonded pattern was heated to 330–360° F. while a bottom bond roll was heated to 300° F.

The SBL sheet, on the other hand, included threads of an elastic material sandwiched between two polypropylene spunbond layers. The elastic material used was KRATON G2740 S-EB-S block copolymer available from the Shell Oil Company. The SBL sheet had a basis is weight of 2.5 osy. An imprinted, magnesium bond plate was used to bond the SBL sheet to the point unbonded spunbond material.

The resulting structure was in the shape of a finger, with a more rounded region at the top and straight sides tapering outwards, such that the interior width at 3.7 cm from the top was about 1.8 cm. Excess material was trimmed around the seam, leaving a textured finger toothbrush with a pull-on tab (SBL side).

A thin (0.6 cm) strip of SBL was formed into a ring (1.5 cm diameter) with a tail, and thermally bonded to close the ring. The end of the tail (5 cm) was thermally bonded to the pull-on tab of the finger toothbrush to produce a finger toothbrush with a tethered fastening ring. The toothbrush was treated with peppermint oil (5 microliters) and used by a small child.

Example 23

The ability of a dental wipe of the present invention to be applied with an anti-ulcer component was demonstrated. A dental wipe of the present invention was formed as follows. Specifically, a first section made from a point unbonded spunbond laminate material was ultrasonically welded to a stretch-bonded laminate (SBL) sheet using a Branson 920 IW ultrasonic welder. The point unbonded spunbond laminate formed the front of the dental wipe, while the SBL sheet formed the back of the dental wipe.

The point unbonded spunbond laminate was formed by thermally bonding together a first polypropylene spunbond web, a breathable film sheet, and a second polypropylene spunbond web. The breathable film sheet was placed in between the spunbond webs.

The first polypropylene spunbond web had a basis weight of 0.5 osy. The second polypropylene spunbond web had a basis weight of 2.8 osy with an average fiber diameter of 7.05 denier. The breathable film sheet was made from a linear low density polyethylene containing a calcium carbonate filler. The film was stretched in order to create a microporous film. The film had a basis weight of 0.5 osy.

The point unbonded spunbond laminate material was thermally bonded using a point-unbonded pattern that created texture. In particular, circular tufts were formed on the second polypropylene spunbond web side of the laminate. During bonding, a top bond roll having the point-unbonded pattern was heated to 350° F. while a bottom bond roll was heated to 300° F.

The SBL sheet, on the other hand, included threads of an elastic material sandwiched between two polypropylene spunbond layers. The elastic material used was KRATON G2740 S-EB-S block copolymer available from the Shell Oil Company. The SBL sheet had a basis weight of 2.5 osy. An imprinted, magnesium bond plate was used to bond the SBL sheet to the point unbonded spunbond laminate.

The second polypropylene spunbond layer of the point unbonded spunbond material was placed adjacent to the SBL sheet during the ultrasonic welding process, which placed the textured nubs against the SBL sheet. After ultrasonic welding, excess material was trimmed around the edges and the finger glove was inverted to place the seam on the inside and the textured nubs on the outside.

The resulting bonded wipe was in the shape of a finger having a rounded region at the top and straight sides tapering outwards, such that the width of the bond pattern 1 cm from the top was 2.3 cm, and the width at 4.5 cm from the top was 2.8 cm.

Thereafter, tetracycline hydrochloride and peppermint oil (20 microliters) were added to the dental wipe. The tetracycline hydrochloride was obtained from Apothecon, a subsidiary of Bristol-Myers Squibb, in the form of a drug sold as SUMYCIN. The tetracycline hydrochloride was applied to the dental wipe in the form of a solution containing 100 microliters of a 40 mg SUMYCIN/milliliter solution in water.

Example 24

The ability of a dental wipe of the present invention to be applied with the following anti-ulcer component was demonstrated. The dental wipe of Example 1 was treated with metronidazole and peppermint oil (20 microliters). Metronidazole was obtained in the form of a topical gel called METROGEL, which is commercially available from Galderma. 200 mg of METROGEL was applied to the dental wipe, which thereby delivered 1.5 mg of metronidazole to the wipe.

Example 25

The ability of a dental wipe of the present invention to be applied with the following anti-ulcer component was demonstrated. The dental wipe of Example 1 was treated with bismuth subsalicylate which is the active ingredient in PEPTO-BISMOL sold by Procter and Gamble. 300 microliters of PEPTO-BISMOL was applied to the dental wipe, which was subsequently used to clean the mouth of a user.

Example 26

The ability of a dental wipe of the present invention to be applied with the following anti-ulcer components was demonstrated. The dental wipe of Example 1 was treated with a suspension of bismuth subsalicylate (200 microliters of PEPTO-BISMOL), metronidazole (50 mg of METROGEL lotion), tetracycline (10 mg of SUMYCIN), and peppermint oil (20 microliters) were applied to the dental wipe, which was then used to clean the mouth of a user.

Example 27

A point unbonded spunbond laminate material was formed by thermally fusing (using a point-unbonded pattern) three materials: a bicomponent spunbond web (PE/PP, side-by-side, 0.45 osy ), a film (0.0007" CATALLOY film, supplied by Pliant Corporation), and a through-air bonded web (PE/PP, side-by-side, 3.5 osy ), with bond pressure, line speed, and temperature adequate to sustain the desirable level of bonding and texture. In this case, the top patterned roll was heated to 256° F., while the bottom bond roll was heated to 248° F. The resulting point unbonded spunbond laminate sheet was ultrasonically welded to a neck-bonded laminate (NBL) sheet using a Branson 920 IW ultrasonic welder. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

An imprinted, stainless steel bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside. A peppermint flavoring (37 μL) was added to the finger glove, which was subsequently packaged in a laminated packaging material that substantially retained the flavoring over time. After one month, the package was opened and the product used to clean the mouth of an adult.

Example 28

A point unbonded spunbond laminate material was formed by thermally fusing (using a point-unbonded pattern) three materials: a bicomponent spunbond web (PE/PP, side-by-side, 0.45 osy), a film (0.0007" CATALLOY film, supplied by Pliant Corporation), and a through-air bonded web (PE/PP, side-by-side, 3.5 osy), with bond pressure, line speed, and temperature adequate to sustain the desirable level of bonding and texture. In this case, the top patterned roll was heated to 256° F., while the bottom bond roll was heated to 248° F. The resulting point unbonded spunbond laminate sheet was ultrasonically welded to a neck-bonded laminate (NBL) sheet using a Branson 920 IW ultrasonic welder. The neck-bonded laminate contained a 1.0 osy mettlocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

An imprinted, stainless steel bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger toothbrush was inverted to place the seam on the inside and the textured nubs on the outside. A suspension of encapsulated flavors in oil (200 mg of a suspension made up of 300 mg encapsulated wintergreen flavor, available from Flavors of North America, Inc., 220 mg encapsulated natural mint flavor, available from Flavors of North America, Inc., 120 mg xylitol, available from Cultor Corporation, and 2 g sunflower oil) was added to the finger toothbrush. The product was packaged, sealed, and then open 48 hours later to clean the mouth of an adult.

Example 29

Example Number 28 was repeated. Instead of using sunflower oil, however, the encapsulated flavors were combined with food-grade propylene glycol.

Example 30

A point unbonded spunbond laminate material was formed by ultrasonically fusing (using a point-unbonded pattern on a 2" rotary ultrasonic anvil) two materials: a film (0.0007" CATALLOY film, supplied by Pliant Corporation), and through-air bonded web (PE/PP, side-by-side, 3.8 osy ), with bond pressure, power, and line speed adequate to sustain the desirable level of bonding and texture. The through-air bonded web was next to the patterned anvil during the bonding process. The resulting point unbonded spunbond laminate sheet was ultrasonically welded to a neck-bonded laminate (NBL) sheet using a Branson 290 IW ultrasonic welder. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width.

An imprinted, stainless steel bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside. Peppermint oil was added to the finger glove, which was subsequently used to clean the mouth of an adult.

Example 31

A point unbonded spunbond laminate material was formed by ultrasonically fusing (using a point-unbonded pattern on a 2" rotary ultrasonic anvil) two materials: a breathable film sheet (LLDPE/CaCO$_3$)/polypropylene, 1.0 osy) and a through-air bonded web (PE/PP, side-by-side fibers 3.5 osy), with bond pressure, line speed, and temperature adequate to sustain the desirable level of bonding and texture. The resulting point unbonded spunbond laminate sheet was ultrasonically welded to a neck-bonded laminate (NBL) sheet using a Branson 920 IW ultrasonic welder. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width. An imprinted, stainless steel bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside.

Example 32

A point unbonded spunbond laminate material was formed by ultrasonically fusing (using a point-unbonded pattern on a 2" rotary ultrasonic anvil) two through-air bonded webs. Both webs were comprised of bicomponent, PE/PP, side-by-side fibers. The top web, adjacent to the patterned anvil during bonding, was comprised of pentalobal shaped fibers, and had a basis weight of 3.5 osy. The bottom web was comprised of conventional round fibers, and had a basis weight of 3.8 osy. Bond pressure (60 psi) and line speed (80 fpm) were set to ensure adequate bonding, although adjustments to the power could allow for other settings providing nearly equivalent bonding. The resulting point unbonded spunbond laminate sheet was ultrasonically welded to a neck-bonded laminate (NBL) sheet using a Branson 920 IW ultrasonic welder. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width. An imprinted, magnesium bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside.

Example 33

A point unbonded spunbond laminate material was formed by ultrasonically bonding two through-air bonded webs. Both webs were comprised of bicomponent, PE/PP, side-by-side fibers. The depth of the round circles (corresponding the unbonded regions) in the patterned anvil was 0.060". The top web, adjacent to the patterned anvil during bonding, was comprised of pentalobal shaped fibers, and had a basis weight of 3.5 osy. The bottom web was comprised of conventional round fibers, and had a weight of 3.8 osy. Bond pressure (60 psi) and line speed (80 fpm) were set to ensure adequate bonding, although adjustments to the power could allow for other settings providing nearly equivalent bonding. The resulting point unbonded spunbond laminate sheet was ultrasonically welded to a neck-bonded laminate (NBL) sheet using a Branson 920 IW ultrasonic welder. The neck-bonded laminate contained a 1.0 osy metallocene-catalyzed polyethylene film laminated to a pair of opposing polypropylene spunbond facings. The spunbond facings had a basis weight of 0.5 osy prior to being stretched or necked. The spunbond facings were necked to a width corresponding to 42% of their original width. An imprinted, magnesium bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside.

Example 34

A point unbonded spunbond laminate material was formed by ultrasonically bonding two through-air bonded webs. Both webs were comprised of bicomponent, PE/PP, side-by-side fibers. The depth of the round circles (corresponding the unbonded regions) in the patterned anvil was 0.120". The top web, adjacent to the patterned anvil during bonding, was comprised of pentalobal shaped fibers., and had a basis weight of 3.5 osy. The bottom web was comprised of conventional round fibers, and had a basis weight of 3.8 osy. Bond pressure (60 psi) and line speed (80 fpm) were set to ensure adequate bonding, although adjustments to the power could allow for other settings providing nearly equivalent bonding. The resulting point unbonded spunbond laminate sheet was ultrasonically welded to a neck-bonded laminate (NBL) sheet using a Branson 920 IW ultrasonic welder. The neck-bonded laminate contained a 1.0 osy metallocene-catalyzed polyethylene film laminated to a pair of opposing polypropylene spunbond facings. The spunbond facings had a weight of 0.5 osy prior to being stretched or necked. The spunbond facings were necked to a width corresponding to 42% of their original width. An imprinted, magnesium bond plate served as the ultrasonic anvil to make the finger-shaped bond pattern. The bicomponent spunbond layer of the point unbonded laminate spunbond material was adjacent to the NBL during the ultrasonic welding process (meaning the textured nubs faced and were pressed against the SBL sheet during welding). After ultrasonic welding, excess material was trimmed around the edges, and the finger glove was inverted to place the seam on the inside and the textured nubs on the outside.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A finger glove comprising:
   a hollow member having an open end for the insertion of a finger, said hollow member comprising a first panel attached to a second panel, said first panel comprising a nonwoven material, said second panel comprising an elastic nonwoven material, said first panel being connected to said second panel in a manner that forms a seam, said seam including a plurality of spaced apart microcuts.

2. A finger glove as defined in claim 1, wherein said first panel includes a texturized surface.

3. A finger glove as defined in claim 2, wherein said texturized surface comprises looped bristles.

4. A finger glove as defined in claim 2, wherein said texturized surface comprises a point unbonded material, said point unbonded material comprising a plurality of raised tufts surrounded by bonded regions.

5. A finger glove as defined in claim 1, wherein said elastic nonwoven material comprises a stretch bonded laminate.

6. A finger glove as defined in claim 1, wherein said elastic nonwoven material comprises a neck bonded laminate.

7. A finger glove as defined in claim 1, wherein said hollow member has been inverted such that said seam is located on the inside of said glove.

8. A finger glove as defined in claim 1, wherein said nonwoven material comprises a laminate including a moisture barrier layer positioned in between a first nonwoven web and a second nonwoven web.

9. A finger glove as defined in claim 1, wherein said elastic nonwoven material comprises an elastic material positioned in between a first nonwoven web and a second nonwoven web.

10. A finger glove as defined in claim 1, wherein the microcuts are spaced less than about 0.5 cm apart.

11. A finger glove as defined in claim 1, wherein the microcuts are at least 0.1 cm in length.

12. A cleaning device comprising:
    a first hollow member having an open end for the insertion of a first finger, the hollow member further defining a texturized surface configured to clean the teeth and gums of a user, said texturized surface having projections in the z-direction, wherein the texturized surface comprises a point unbonded material, the point unbonded material comprising a plurality of raised tufts surrounded by bonded regions;
    a second hollow member having an open end for the insertion of a second finger, at least the first hollow member or the second hollow member containing an elastic nonwoven comprising an elastic component and a non-elastic component; and
    a connecting portion for connecting the first hollow member to the second hollow member.

13. A cleaning device as defined in claim 12, wherein the first hollow member and the second hollow member both comprise an elastic nonwoven material.

14. A cleaning device as defined in claim 12, wherein the second hollow member defines a texturized surface.

15. A cleaning device as defined in claim 12, wherein the texturized surface comprises looped bristles.

16. A cleaning device as defined in claim 13, wherein the elastic nonwoven material of the first hollow member and of the second hollow member comprises an elastic component and a non-elastic component.

17. A cleaning device as defined in claim 12, wherein the first hollow member and the second hollow member include a closed end located opposite each open end.

18. A cleaning device as defined in claim 13, wherein at least the elastic nonwoven material of the first hollow member or the elastic nonwoven material of the second hollow member comprises a stretch bonded laminate.

19. A cleaning device as defined in claim 13, wherein at least the elastic nonwoven material of the first hollow member or the elastic nonwoven material of the second hollow member comprises a neck-bonded laminate.

20. A cleaning device as defined in claim 12, wherein the first hollow member includes a first panel attached to a second panel, the first panel comprising an elastic nonwoven material, while the second panel comprises a non-elastic material.

21. A cleaning device as defined in claim 20, wherein the second hollow member also includes a first panel attached to a second panel, the first panel comprising an elastic nonwoven material, while the second panel comprises a non-elastic material.

22. A cleaning device as defined in claim 12, wherein an additive has been applied to the cleaning device, the additive comprising a material selected from the group consisting of cationic materials, fluorides, flavoring agents, and mixtures thereof.

23. A cleaning device as defined in claim 22, wherein the connecting portion comprises dental floss.

* * * * *

UNITED STATES PATENT AND TRADEMARK OFFICE
CERTIFICATE OF CORRECTION

PATENT NO. : 7,127,771 B2  
APPLICATION NO. : 10/603043  
DATED : October 31, 2006  
INVENTOR(S) : McDevitt et al.

Page 1 of 1

It is certified that error appears in the above-identified patent and that said Letters Patent is hereby corrected as shown below:

On the title page item (60)

"Provisional application No. 60/257,173, filed on Dec...." should read --Provisional application No. 60/257,137, filed on Dec....--

Signed and Sealed this
Twenty-fifth Day of August, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 7,127,771 B2 | Page 1 of 1 |
| APPLICATION NO. | : 10/603043 | |
| DATED | : October 31, 2006 | |
| INVENTOR(S) | : McDevitt et al. | |

It is certified that error appears in the above-identified patent and that said Letters Patent is hereby corrected as shown below:

On the title page item (60)

"Provisional application No. 60/257,173, filed on Dec...." should read --Provisional application No. 60/257,137, filed on Dec....--

In the specification

Column 1, line 13, delete "60/257,173" and insert --60/257,137--

This certificate supersedes the Certificate of Correction issued August 25, 2015.

Signed and Sealed this
Nineteenth Day of January, 2016

Michelle K. Lee
*Director of the United States Patent and Trademark Office*